United States Patent
Jang

(10) Patent No.: US 11,837,326 B2
(45) Date of Patent: Dec. 5, 2023

(54) METHODS FOR PREPARING OLIGONUCLEOTIDES FOR DETECTING TARGET NUCLEIC ACID SEQUENCES WITH A MAXIMUM COVERAGE

(71) Applicant: SEEGENE, INC., Seoul (KR)

(72) Inventor: Mi Hyun Jang, Seoul (KR)

(73) Assignee: SEEGENE, INC., Seoul (KR)

( * ) Notice: Subject to any disclaimer, the term of this patent is extended or adjusted under 35 U.S.C. 154(b) by 988 days.

(21) Appl. No.: 16/633,279

(22) PCT Filed: Aug. 10, 2018

(86) PCT No.: PCT/KR2018/009178
§ 371 (c)(1),
(2) Date: Jan. 23, 2020

(87) PCT Pub. No.: WO2019/031916
PCT Pub. Date: Feb. 14, 2019

(65) Prior Publication Data
US 2020/0152290 A1 May 14, 2020

(30) Foreign Application Priority Data
Aug. 11, 2017 (KR) .......................... 10-2017-0102502

(51) Int. Cl.
*G16B 30/00* (2019.01)
*G16B 20/00* (2019.01)

(52) U.S. Cl.
CPC ............. *G16B 30/00* (2019.02); *G16B 20/00* (2019.02)

(58) Field of Classification Search
CPC ................................ G16B 30/00; G16B 20/00
See application file for complete search history.

(56) References Cited

U.S. PATENT DOCUMENTS

| | | |
|---|---|---|
| 8,318,423 B2 | 11/2012 | Lee et al. |
| 8,685,649 B2 | 4/2014 | Dauner et al. |
| 8,735,063 B2 | 5/2014 | Beld et al. |
| 2007/0259337 A1 | 11/2007 | Hully et al. |
| 2009/0198479 A1 | 8/2009 | Bulla, Jr. et al. |
| 2017/0053061 A1 | 2/2017 | Almonacid et al. |

OTHER PUBLICATIONS

Najafabadi, H. S. et al., "Designing multiple degenerate primers via consecutive pairwise alignments", BMC Bioinformatics, Jan. 27, 2008, vol. 9, No. 55, pp. 1-8.

Najafabadi, H. S. et al., "MAD-DPD: designing highly degenerate primers with maximum amplification specificity with maximum amplification specificity", BioTechniques, Apr. 2008, vol. 44, pp. 519-526.

Kalendar, R. et al., "FastPCR: An in silico tool for fast primer and probe design and advanced sequence analysis", Genomics, Epub. May 12, 2017, vol. 109, pp. 312-319.

Nathalie Bastien et al., "Genetic Variability of the G Glycoprotein Gene of Human Metapneumovirus" Journal of Clinical Microbiology, Aug. 2004, p. 3532-3537.

Teresa C. T. Peret et al., "Characterization of Human Metapneumoviruses Isolated from Patients in North America" The Journal of Infectious Diseases 2002;185:1660-3.

Takashi Ebihara et al., "Human Metapneumovirus Infection in Japanese Children" Journal of Clinical Microbiology, Jan. 2004, p. 126-132.

Elizabeth R. Jenny-Avital et al., "Erroneously Low or Undetectable Plasma Human Immunodeficiency Virus Type 1 (HIV-1) Ribonucleic Acid Load, Determined by Polymerase Chain Reaction, in West African and American Patients with Non-B Subtype HIV-1 Infection" Clinical Infectious Diseases 2001; 32:1227-30.

Duffy, S., et al., "Rates of evolutionary change in viruses: patterns and determinants", Nature Reviews, Genetics, vol. 9, Apr. 2008, pp. 267-276.

Tong, Y. G., et al., "Genetic diversity and evolutionary dynamics of Ebola virus in Sierra Leone", Research Letter, 2015, pp. 1-11.

Tong, Y. G., et al., "Genetic diversity and evolutionary dynamics of Ebola virus in Sierra Leone", Research Letter, Corrections and Amendments, 2015, p. 1.

International Search Report from corresponding PCT/KR2018/009178, dated Mar. 22, 2019.

Kelvin Li et al: "Automated degenerate PCR primer design for high-throughput sequencing improves efficiency of viral sequencing" Nov. 6, 2012.

Li Kelvin et al: "ANDES: Statistical tools for the ANalyses of DEep Sequencing" Jul. 15, 2010.

Macleod Iain J, et al: "Abstract", bioRxiv, Oct. 29, 2019.

Supplementary Search Report from European Patent Application No. EP18844370.

*Primary Examiner* — Jerry Lin
(74) *Attorney, Agent, or Firm* — Harness, Dickey & Pierce, P.L.C.

(57) ABSTRACT

The present invention relates to optimization logic for preparing an optimal introduction of degenerate bases and/or universal bases into an oligonucleotide used to detect a plurality of target nucleic acid sequences, in a completely different approach from conventional methods, i.e., empirical and manual methods. In addition, the optimization logic of the present invention may be used in (i) the preparation of an oligonucleotide into which a limited number of degenerate bases and/or universal bases are introduced for detecting a plurality of target nucleic acid sequences with a maximum target coverage, and (ii) the determination of a probing region in a plurality of target nucleic acid sequences.

23 Claims, 3 Drawing Sheets
Specification includes a Sequence Listing.

Fig. 1

$$A = (a_{ij}) = \begin{bmatrix} 1 & 0 & 1 & 1 & 0 & 1 & 1 & 1 & 1 & 1 & 1 & 1 & 1 & 1 & 1 & 1 & 0 & 1 \\ 1 & 0 & 1 & 1 & 1 & 0 & 1 & 1 & 1 & 1 & 1 & 1 & 1 & 1 & 1 & 1 & 1 & 0 \\ 1 & 0 & 1 & 1 & 1 & 1 & 1 & 1 & 1 & 1 & 1 & 1 & 1 & 1 & 1 & 1 & 1 & 1 \\ 1 & 1 & 0 & 1 & 1 & 1 & 1 & 1 & 1 & 1 & 1 & 0 & 1 & 1 & 1 & 1 & 1 & 1 \\ 1 & 1 & 0 & 1 & 1 & 1 & 1 & 1 & 1 & 1 & 1 & 1 & 1 & 1 & 1 & 1 & 1 & 1 \\ 1 & 1 & 1 & 0 & 1 & 1 & 1 & 1 & 1 & 1 & 1 & 0 & 1 & 1 & 1 & 1 & 1 & 1 \\ 1 & 1 & 1 & 1 & 0 & 1 & 1 & 0 & 1 & 1 & 1 & 1 & 1 & 1 & 1 & 1 & 1 & 1 \\ 1 & 1 & 1 & 1 & 1 & 0 & 1 & 1 & 1 & 1 & 1 & 1 & 1 & 1 & 1 & 1 & 1 & 0 \\ 1 & 1 & 1 & 1 & 1 & 1 & 0 & 0 & 1 & 0 & 1 & 1 & 1 & 1 & 1 & 1 & 1 & 1 \\ 1 & 1 & 1 & 1 & 1 & 1 & 0 & 1 & 1 & 1 & 1 & 0 & 1 & 1 & 1 & 1 & 1 & 1 \\ 1 & 1 & 1 & 1 & 1 & 1 & 1 & 0 & 1 & 1 & 1 & 1 & 1 & 1 & 0 & 1 & 1 & 0 \\ 1 & 1 & 1 & 1 & 1 & 1 & 1 & 0 & 1 & 1 & 1 & 1 & 1 & 1 & 1 & 0 & 1 & 1 \\ 1 & 1 & 1 & 1 & 1 & 1 & 1 & 1 & 1 & 0 & 1 & 1 & 1 & 1 & 1 & 0 & 1 & 1 \\ 1 & 1 & 1 & 1 & 1 & 1 & 1 & 1 & 1 & 0 & 1 & 1 & 1 & 1 & 1 & 1 & 1 & 1 \\ 1 & 1 & 1 & 1 & 1 & 1 & 1 & 1 & 1 & 1 & 1 & 0 & 1 & 1 & 1 & 1 & 1 & 1 \\ 1 & 1 & 1 & 1 & 1 & 1 & 1 & 1 & 1 & 1 & 1 & 1 & 1 & 1 & 0 & 0 & 0 & 0 \\ 1 & 1 & 1 & 1 & 1 & 1 & 1 & 1 & 1 & 1 & 1 & 1 & 1 & 1 & 1 & 0 & 1 & 0 \\ 1 & 1 & 1 & 1 & 1 & 1 & 1 & 1 & 1 & 1 & 1 & 1 & 1 & 1 & 1 & 0 & 1 & 1 \\ 1 & 1 & 1 & 1 & 1 & 1 & 1 & 1 & 1 & 1 & 1 & 1 & 1 & 1 & 1 & 1 & 0 & 1 \\ 1 & 1 & 1 & 1 & 1 & 1 & 1 & 1 & 1 & 1 & 1 & 1 & 1 & 1 & 1 & 1 & 1 & 1 \end{bmatrix}$$

METHODS FOR PREPARING OLIGONUCLEOTIDES FOR DETECTING TARGET NUCLEIC ACID SEQUENCES WITH A MAXIMUM COVERAGE

CROSS-REFERENCE TO RELATED APPLICATIONS

This application is a national phase application of PCT Application No. PCT/KR2018/009178 filed on Aug. 10, 2018, which claims priority to Korean Patent Application No. 10-2017-0102502 filed on Aug. 11, 2017. The entire disclosures of the applications identified in this paragraph are incorporated herein by reference.

BACKGROUND OF THE INVENTION

Field of the Invention

The present invention relates to technologies for preparing an oligonucleotide for detecting a plurality of target nucleic acid sequences having sequence similarity with a maximum target coverage, and for determining a probing region in a plurality of target nucleic acid sequences having sequence similarity.

Description of the Related Art

A variety of techniques have been developed to detect target nucleic acid molecules of pathogens and identify these target nucleic acid molecules, and these are collectively referred to as molecular diagnostics. Most of the molecular diagnostic techniques use oligonucleotides such as primers and probes hybridizable with target nucleic acid molecules.

To date, molecular diagnostic technologies have made many advances. However, there are still technical challenges to be solved in the diagnosis of pathogens having genomes that exhibit genetic diversity or genetic variability.

Genetic diversity or genetic variability has been reported in various genomes. In particular, genetic diversity is most frequently found and occurs in viral genomes (Bastien N. et al., Journal of Clinical Microbiology, 42:3532(2004); Peret T C. et al., Journal of Infectious Diseases, 185:1660(2002); Ebihara T. et al., Journal of Clinical Microbiology, 42:126 (2004); Jenny-Avital E R. et al. Clinical Infectious Diseases, 32:1227(2001); Duffy S. et. al., Nat. Rev. Genet. 9(4):267-76(2008); Tong Y G et. al., Nature. 22:526(2015)).

In detecting a pathogen with genetic diversity, designing oligonucleotides with taking into account a certain sequence of a target nucleic acid molecule of this pathogen is very likely to lead to false negative results. Thus, in order to determine whether a certain pathogen is present in an unknown sample, probes or primers should be designed in consideration of all nucleic acid sequences or as many nucleic acid sequences as possible of known genetic diversity for one target nucleic acid molecule of this certain pathogen. In order to detect a target nucleic acid molecule exhibiting such genetic diversity, two approaches have been largely developed.

The first method detects a target nucleic acid molecule using a plurality of oligonucleotides that are hybridized with a plurality of nucleic acid sequences of a target nucleic acid molecule exhibiting genetic diversity. For example, when targeting M gene of influenza A virus, all nucleic acid sequences known to the M gene are aligned and probes are designed being capable of covering all of these nucleic acid sequences. In this case, since a single probe cannot cover all M genes of various sequences, a plurality of probes (probes with different probing positions each other) are designed.

The second method is to design a degenerate oligonucleotide. Typically, a region is found in all nucleic acid sequences of a certain gene having genetic diversity, and the certain gene is detected with coverage of interest using a degenerate primer or probe (including a degenerate base at a variation site) that is hybridized with the region (see, U.S. Pat. Nos. 8,735,063, 8,318,423, and 8,685,649).

For the second approach, it is most important to optimally apply degenerate bases to the oligonucleotide used to detect various nucleic acid sequences of a target nucleic acid molecule with diversity. Taking into consideration convenience, efficiency and economy of an analysis, it is desirable to detect a target nucleic acid molecule with a maximum target coverage using the oligonucleotide to which the degenerate bases are optimally applied.

Conventionally, in order to detect various nucleic acid sequences of a target nucleic acid molecule with genetic diversity, researchers have determined introduction positions and number of degenerate bases for maximally covering a plurality of nucleic acid sequences by applying degenerate bases to a probe in a sequential or random manner.

The conventional approach in which a limited number of degenerate bases are sequentially or randomly applied to certain positions of probes for determining to maximally cover sequences may be proposed when the number of target nucleic acid sequences is small. However, where the number of target nucleic acid sequences becomes much larger and degenerate oligonucleotides covering sequences maximally are demanded, the conventional approach has serious shortcomings in light of the fact that it not only takes a long time but also have poor accuracy.

To our best knowledge, there is no prior art to solve the technical problem to be achieved in the present invention by an optimization logic, namely, (i) preparing an oligonucleotide for detecting a plurality of target nucleic acid sequences having sequence similarity with a maximum target coverage, and (ii) determining a probing region in a plurality of target nucleic acid sequences having sequence similarity.

Throughout this application, various patents and publications are referenced and citations are provided in parentheses. The disclosure of these patents and publications in their entireties are hereby incorporated by references into this application in order to more fully describe this invention and the state of the art to which this invention pertains.

SUMMARY OF THE INVENTION

The present inventor has made intensive researches to develop technologies for optimally applying degenerate bases and/or universal bases to oligonucleotides to maximally cover a plurality of target nucleic acid sequences, inter alia, a plurality of nucleic acid sequences (particularly, target nucleic acid sequences) of a target nucleic acid molecule exhibiting genetic diversity, with more improved speed and accuracy. As a result, the present inventor has developed optimization logic for an optimal introduction of degenerate bases and/or universal bases into an oligonucleotide (e.g., a probe and a primer) used to detect a plurality of target nucleic acid sequences, in a completely different approach from conventional methods, i.e., empirical and manual methods. In addition, the present inventor has found that the optimization logic may be used in (i) preparing an oligonucleotide for detecting a plurality of target nucleic acid sequences having sequence similarity with a maximum target coverage, and (ii) determining a probing region in a plurality of target nucleic acid sequences having sequence similarity.

Accordingly, it is an object of this invention to provide a method for preparing an oligonucleotide for detecting a plurality of target nucleic acid sequences having sequence similarity with a maximum target coverage.

It is another object of this invention to provide a method for determining a probing region in a plurality of target nucleic acid sequences having sequence similarity.

It is still another object of this invention to provide a computer readable storage medium containing instructions to configure a processor to perform a method for preparing an oligonucleotide for detecting a plurality of target nucleic acid sequences having sequence similarity with a maximum target coverage.

It is another object of this invention to provide a computer readable storage medium containing instructions to configure a processor to perform a method for determining a probing region in a plurality of target nucleic acid sequences having sequence similarity.

Other objects and advantages of the present invention will become apparent from the detailed description to follow taken in conjugation with the appended claims and drawings.

BRIEF DESCRIPTION OF THE DRAWINGS

FIG. 1 shows a binary matrix ($A=\{a_{i,j}, a_{i,j} \in (0, 1)\}$) consisting of a matching value and a non-matching value indicating whether or not probes having various sequence patterns are matched with a reference probe (reference oligonucleotide) according to an embodiment of the present invention.

DETAILED DESCRIPTION OF THIS INVENTION

Figure 2:
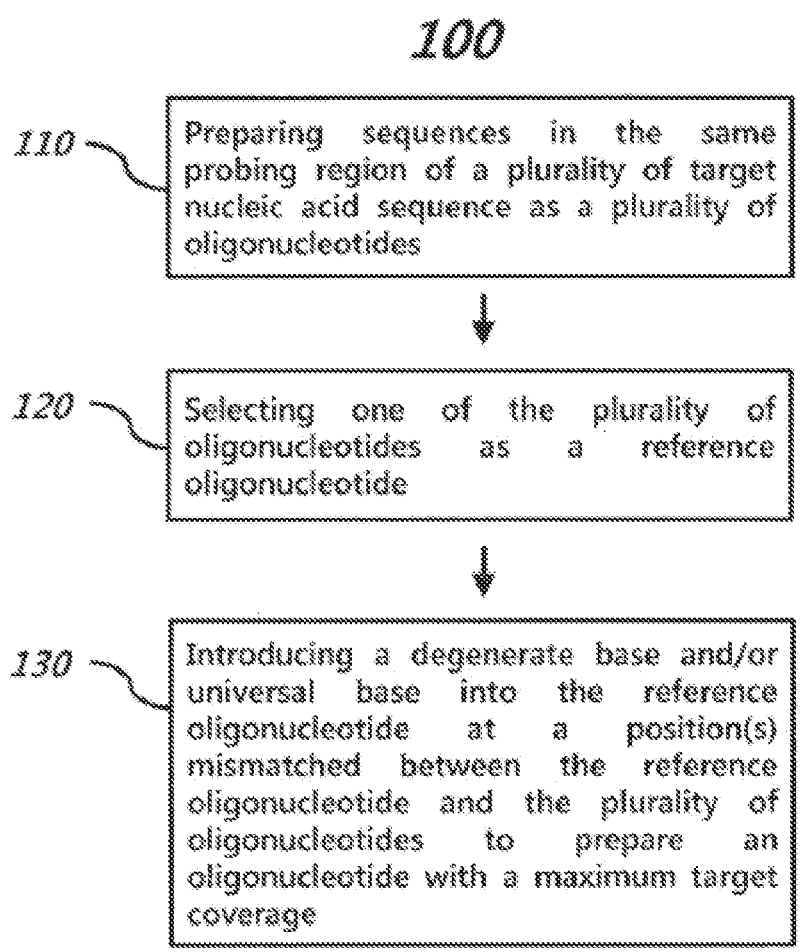
FIG. 2 is a flow diagram representing a process of preparing an oligonucleotide for detecting a plurality of target nucleic acid sequences having sequence similarity with a maximum target coverage according to an embodiment of the present invention.

The technical purpose of the present invention is to efficiently make decisions that may be encountered to analysts in simultaneously detecting a plurality of target nucleic acid sequences, particularly a plurality of target nucleic acid sequences having sequence similarity, particularly (i) determining an optimal introduction of degenerate bases and/or universal bases into an oligonucleotide for detecting a plurality of target nucleic acid sequences with a maximum target coverage, and (ii) determining a probing region in a plurality of target nucleic acid sequences.

The inventors have developed two most ideal optimization logics for these decisions. These logics share common features and therefore the present invention is largely divided into two aspects. Hereinafter, the present invention will be described in detail.

I. Preparation of an Oligonucleotide to Detect a Plurality of Target Nucleic Acid Sequences with a Maximum Target Coverage In one aspect of the present invention, there is provided a method for preparing an oligonucleotide for detecting a plurality of target nucleic acid sequences having sequence similarity with a maximum target coverage, comprising: (a) selecting each of sequences with sequence similarity in the same probing region of a plurality of target nucleic acid sequences as a probing sequence or an oligonucleotide sequence to prepare a plurality of probing sequences or a plurality of oligonucleotides; (b) selecting one of the plurality of probing sequences as a reference probing sequence or one of the plurality of oligonucleotides as a reference oligonucleotide; and (c) introducing a degenerate base and/or universal base in a predetermined allowable number into the reference probing sequence or the reference oligonucleotide at a position(s) mismatched between (i) the reference probing sequence or the reference oligonucleotide and (ii) the plurality of probing sequences or the plurality of oligonucleotides to be maximally matched with the plurality of probing sequences or the plurality of oligonucleotides, and selecting as a sequence of an oligonucleotide the reference probing sequence or a sequence of the reference oligonucleotide into which at least one of the degenerate base and/or the universal base is introduced, thereby preparing an oligonucleotide with a maximum target coverage.

A first aspect of the present invention relates to a method for preparing an optimal introduction of a degenerate base and/or universal base in a predetermined allowable number into an oligonucleotide (e.g., a probe and a primer) used to detect a plurality of target nucleic acid sequences with a maximum target coverage. In other words, the first method of the present invention is an optimization method that maximizes the target coverage of an oligonucleotide for the target nucleic acid sequence to be detected, given a limited number of the degenerate base and/or universal base to be introduced into the oligonucleotide.

The term "a predetermined allowable number" or "a limited number" used herein with referring to the number of degenerate base and/or universal base means detecting a plurality of target nucleic acid sequences with a maximum target coverage by introducing a predetermined allowable number or less or a limited number or less of degenerate base and/or universal base into the oligonucleotide. For example, the limited number of degenerate base and/or universal base to be introduced into the oligonucleotide of 3 represents detecting a plurality of target nucleic acid sequences with a maximum target coverage by introducing three or less of degenerate base and/or universal base into the oligonucleotide.

FIG. 2 is a flow diagram of the procedures for performing the invention in accordance with an embodiment of the invention. The method of the present invention will be described with reference to FIG. 2:

Step (a): Preparing a Plurality of Probing Sequences or Oligonucleotides (110)

First, a plurality of probing sequences or a plurality of oligonucleotides are prepared by selecting each of sequences with sequence similarity in the same probing region of a plurality of target nucleic acid sequences as a probing sequence or an oligonucleotide sequence. A plurality of probing sequences or plurality of oligonucleotides are selected as a reference probe sequence or a reference oligonucleotide in step (b), and their sequences are considerable factors when determining an optimal introduction of the degenerate base and/or universal base into the reference probe sequence or the reference oligonucleotide in the step (c).

The term used herein "target nucleic acid molecule", "target molecule" or "target nucleic acid" means a nucleotide molecule in an organism intended to detect. Generally, the target nucleic acid molecule has a certain name and includes an entire genome and all nucleotide molecules that make up a genome (e.g., gene, pseudo gene, non-coding sequence molecule, untranslated region and some regions of genome).

The target nucleic acid molecule includes, for example, prokaryotic cell (e.g., *Mycoplasma pneumoniae, Chlamydophila pneumoniae, Legionella pneumophila, Haemophilus influenzae, Streptococcus pneumoniae, Bordetella pertussis, Bordetella parapertussis, Neisseria meningitidis, Listeria monocytogenes, Streptococcus agalactiae, Campylobacter, Clostridium difficile, Clostridium perfringens, Salmonella, Escherichia coli, Shigella, Vibrio, Yersinia enterocolitica, Aeromonas, Chlamydia trachomatis, Neisseria gonorrhoeae, Trichomonas vaginalis; Mycoplasma Mycoplasma genitalium, Ureaplasma urealyticum, Ureaplasma parvum, Mycobacterium tuberculosis*) nucleic acid, eukaryotic cell (e.g., protozoan and parasitic animal, fungus, yeast, higher plant, lower animal, and higher animal including mammal and human) nucleic acid, virus nucleic acid or viroid nucleic acid. Parasite of the eukaryotic cell includes, for example, *Giardia lamblia, Entamoeba histolytica, Cryptosporidium, Blastocystis hominis, Dientamoeba fragilis, Cyclospora cayetanensis*. Example of such virus includes influenza A virus (Flu A), influenza B virus (Flu B), respiratory syncytial virus A (RSV A), respiratory syncytial virus B (RSV B), parainfluenza virus 1 (PIV 1), parainfluenza virus 2 (PIV 2), parainfluenza virus 3 (PIV 3), parainfluenza virus 4 (PIV 4), metapneumovirus (MPV), human enterovirus (HEV), human bocavirus (HBoV), human rhinovirus (HRV), coronavirus and adenovirus, which cause respiratory diseases; norovirus, rotavirus, adenovirus, astrovirus, and sapovirus, which cause gastrointestinal disorders. The virus also includes, for example, human papillomavirus (HPV), middle east respiratory syndrome-related coronavirus (MERS-CoV), dengue virus, herpes simplex virus (HSV), human herpes virus (HHV), epstein-barr virus (EMV), varicella zoster virus (VZV), cytomegalovirus (CMV), HIV, hepatitis virus and poliovirus.

The term used herein "target nucleic acid sequence" or "target sequence" represents a target nucleic add molecule as a certain sequence.

One target nucleic acid molecule, e.g., one target gene, may have a certain target nucleic acid sequence; otherwise for a target nucleic acid molecule exhibiting genetic diversity or genetic variability, it may have a plurality of target nucleic acid sequences with diversity. When it is intended to detect a target nucleic acid molecule exhibiting genetic diversity without a false negative result, the combination of a plurality of oligonucleotides or an oligonucleotide into which degenerate bases and/or universal bases are introduced being capable of covering a plurality of target nucleic acid sequences with diversity are usually required.

The plurality of target nucleic acid sequences in the present invention are target nucleic acid sequences having sequence similarity. Particularly, the target nucleic acid sequences having sequence similarity may be a plurality of target nucleic acid sequences of one target nucleic acid molecule or a plurality of target nucleic acid sequences of two or more target nucleic acid molecules.

According to an embodiment, the plurality of target nucleic acid sequences in the present invention are a plurality of nucleic acid sequences having sequence similarity for one target nucleic acid molecule having genetic diversity.

For example, the plurality of target nucleic acid sequences used in the present invention are a plurality of nucleic acid sequences having sequence similarity for a target nucleic acid molecule that exhibits genetic diversity such as a viral genome sequence. For example, when influenza A virus is intended to detect and the M gene is determined as a target nucleic acid molecule, target nucleic acid sequences with diversity of the M gene of influenza A virus may be used. Influenza A virus includes a variety of subtypes and variants, and their genomic sequences are different from each other. Therefore, when influenza A virus is intended to detect without a false negative result, an oligonucleotide should be designed considering various target nucleic acid sequences of a target nucleic acid molecule of influenza A virus originated from such genetic diversity.

More particularly, the plurality of target nucleic acid sequences are a whole genome sequence, a partial sequence of a genome, or a plurality of nucleic acid sequences of one gene of virus or bacteria having genetic diversity.

According to an embodiment of the present invention, the plurality of target nucleic acid sequences are a plurality of nucleic acid sequences corresponding to homologues of organisms having the same function, the same structure, or the same gene name. The organism refers to an organism belonging to one genus, species, subspecies, subtype, genotype, serotype, strain, isolate or cultivar. The homologues include proteins and nucleic acid molecules. In this embodiment, a plurality of nucleic acid sequences of homologous biomolecules (e.g., protein or nucleic acid) of a plurality of organisms having the same function (e.g., a biological function of a protein encoded by a nucleic acid sequence), the same structure (e.g., a tertiary structure of a protein encoded by a nucleic acid sequence) or the same gene name are used. For example, a plurality of nucleic acid sequences known for the E5 gene of HPV type 16 may be considered as a nucleic acid sequence of isolates of HPV type 16. When the E5 gene is used as a target nucleic acid molecule for detecting HPV type 16, degenerate bases and/or universal bases should be introduced into an oligonucleotide to be capable of covering a plurality of nucleic acid sequences with diversity of the E5 gene of HPV type 16.

According to one embodiment, the target nucleic acid sequence comprises nucleic acid sequences belonging to a subclass of any biological classification (e.g., genus, species, subtype, genotype, serotype and subspecies). For example, when the target nucleic acid sequence is HPV type 16, the target nucleic acid sequence may comprise nucleic acid sequences belonging to that subclass.

According to an embodiment of the present invention, the plurality of target nucleic acid sequences are at least 3, at least 5, at least 10, at least 20, at least 30, at least 40, at least 50, at least 60, at least 70, at least 80, at least 90 or at least 100 nucleic acid sequences.

A plurality of target nucleic acid sequences may be provided using various sequence databases. For example, a plurality of desired target nucleic acid sequences may be collected and provided from a publicly accessible database such as GenBank, European Molecular Biology Laboratory (EMBL) sequence database, and DNA DataBank of Japan (DDBJ).

According to an embodiment, a plurality of target nucleic acid sequences are aligned prior to the step (a). Alignment of target nucleic acid sequences may be performed according to various methods (e.g., global alignment and local alignment) and algorithms known in the art.

Various methods and algorithms for alignment are described in Smith and Waterman, *Adv. Appl. Math.* 2:482 (1981); Needleman and Wunsch, *J. Mol. Bio.* 48:443(1970); Pearson and Lipman, Methods in Mol. Biol. 24: 307-31 (1988); Higgins and Sharp, Gene 73:237-44(1988); Higgins and Sharp, *CABIOS* 5:151-3(1989); Corpet et al., *Nuc. Acids Res.* 16: 10881-90 (1988); Huang et al., *Comp. Appl. BioSci.* 8:155-65(1992) and Pearson et al., *Meth. Mol, Biol.* 24:307-31(1994). The NCBI Basic Local Alignment Search Tool (BLAST) (Altschul et al., *J. Mol, Biol.* 215:403-10(1990)) is accessible from NCBI (National Center for Biological Information) and may be used in conjunction with sequence analysis programs such as blastn, blasm, blastx, tblastn and tblastx on the Internet. BLAST is available at ncbi.nlm.nih.gov/BLAST/. A comparison of sequence similarity using this program may be found at ncbi.nlm.nih.gov/BLAST/blast.

According to the present invention, the plurality of target nucleic acid sequences are aligned and each of the sequences having sequence similarity in the same probing region is selected as a probing sequence or an oligonucleotide sequence.

The term used herein "probing region" refers to one region of the target nucleic acid sequence suitable for target-specific hybridization of oligonucleotides such as primers and probes, and the term encompasses a priming region.

For example, when there are 10 target nucleic acid sequences from A to J, the target nucleic acid sequences from A to J are aligned and sequences of the same region in a certain length having sequence similarity are selected as probing sequences of target nucleic acid sequences from A to J.

According to one embodiment of the invention, the probing regions with sequence similarity suitable for being selected as the probing sequences have 20-100%, 30-100%, 40-100%, 50-100%, 60-100%, 70-100%, 80-100% or 90-100% sequence similarity.

Each of the sequences having sequence similarity in the same probing region may be selected as a probing sequence for each of a plurality of target nucleic acid sequences and may also be selected as an oligonucleotide sequence. In this Specification, oligonucleotides except an oligonucleotide showing a maximum target coverage finally prepared in step (c) are those used for the preparation of the oligonucleotide showing a maximum target coverage. The sequences of these oligonucleotides may comprise sequences that are hybridized with probing sequences or hybridized with their complementary sequences. When the oligonucleotides are sequences that are hybridized with complementary sequences to probing sequences, the probing sequences may be oligonucleotide sequences. That is, the oligonucleotide having a maximum target coverage finally prepared may be provided using a plurality of probing sequences or a plurality of oligonucleotides.

According to an embodiment of the present invention, the plurality of probing sequences or oligonucleotides each has a unique serial number.

Step (b): Selecting a Reference Probing Sequence or Oligonucleotide (120)

Then, one of the plurality of probing sequences or one of the plurality of oligonucleotides is selected as a reference probing sequence or a reference oligonucleotide, respectively.

The selected reference probing sequence or reference oligonucleotide is a reference for determining whether to be matched with (i) the plurality of probing sequences or (ii) the plurality of oligonucleotides in step (c), and is an introduction subject in introducing a degenerate base and/or universal base at a position(s) mismatched between them.

For this purpose, a reference probing sequence or a reference oligonucleotide may be used by selecting any one of the plurality of probing sequences or any one of the plurality of oligonucleotides.

According to an embodiment, the reference probing sequence is a probing sequence having the largest number of identical sequences among the plurality of probing sequences and the reference oligonucleotide is an oligonucleotide having the largest number of identical sequences among the plurality of oligonucleotides.

Because the oligonucleotide provided by the present invention are prepared by optimally introducing a degenerate base and/or universal base to detect a plurality of target nucleic acid sequences with a maximum target coverage, it is desirable that the probing sequence having the largest number of identical sequences among the plurality of probing sequences or the oligonucleotide having the largest number of identical sequences among the plurality of oligonucleotides is selected as the reference probing sequence or the reference oligonucleotide.

Step (c): Preparing an Oligonucleotide with a Maximum Target Coverage (130)

Then, an oligonucleotide with a maximum target coverage is prepared by introducing a degenerate base and/or universal base in a predetermined allowable number into the reference probing sequence or the reference oligonucleotide at a position(s) mismatched between (i) the reference probing sequence or the reference oligonucleotide and (ii) the plurality of probing sequences or the plurality of oligonucleotides to be maximally matched with the plurality of probing sequences or the plurality of oligonucleotides, and selecting as a sequence of an oligonucleotide the reference probing sequence or a sequence of the reference oligonucleotide into which at least one of the degenerate base and/or the universal base is introduced.

In the present invention, for determining the position(s) into which at least one of the degenerate base and/or the universal base is introduced, the reference for comparison is either the reference probing sequence or the reference oligonucleotide and the subject of comparison is (ii) a plurality of probing sequences or a plurality of oligonucleotides. Thus, in the present invention, the comparison of a match or mismatch for introducing the degenerate base and/or universal base may be performed in four forms, particularly, between a reference probing sequence and a plurality of probing sequences, between a reference probing sequence and a plurality of oligonucleotides, between a reference oligonucleotide and a plurality of probing sequences, or between a reference oligonucleotide and a plurality of oligonucleotides.

The term "mismatch" used herein with referring to the position(s) of introduction of the degenerate base and/or universal base means that two bases corresponding to the same position of two sequences are not identical when the direction of the two sequences for comparison is the same, and two corresponding bases of the two sequences are non-complementary when the direction is different. For example, when a sequence of the reference oligonucleotide as a reference for mismatch comparison and the plurality of probing sequences as a subject of comparison both have a direction of 5' to 3', and at the same position the reference oligonucleotide has "A" and the probing sequence as the subject of the comparison has a base other than "A", the position becomes a mismatched position. Alternatively, when a sequence of the reference oligonucleotide has a direction of 5' to 3' and the plurality of probing sequences as the subject of comparison have a direction of 3' to 5, and at the same position the reference oligonucleotide has "A" and the probing sequence has a base other than "T", the position becomes a mismatched position.

In the present invention, the degenerate base and/or universal base in a predetermined allowable number is introduced into the reference probing sequence or the reference oligonucleotide at the position(s) mismatched between (i) the reference probing sequence or the reference oligonucleotide and (ii) the plurality of probing sequences or the plurality of oligonucleotides. The subject of introduction of the degenerate base and/or universal base in the present invention is the reference probing sequence or the reference oligonucleotide.

The predetermined allowable number of the degenerate base and/or universal base to be introduced in this invention is particularly 7 or less, 5 or less, 4 or less, or 3 or less. The use rate of the degenerate base and/or universal base to be introduced in this invention is particularly 25% or less, 20% or less, 18% or less, 16% or less, 14% or less, 12% or less, 10% or less, 8% or less, or 6% or less. The use rate of the degenerate base and/or universal base indicates the ratio of a degenerate base and/or universal base among the total nucleotides of the oligonucleotide into which the degenerate base and/or universal base is introduced.

In the present invention, the degenerate base and/or universal base is introduced into the reference probing sequence or the reference oligonucleotide to be maximally matched with the plurality of probing sequences or the plurality of oligonucleotides.

The term "maximum matching" used herein with referring to the introduction of the degenerate base and/or universal base means that the number of the plurality of probing sequences or the plurality of oligonucleotides having the same sequence as the reference probing sequence or the reference oligonucleotide into which the degenerate base and/or universal base is introduced is maximized, and the maximum matching may be expressed as a proportion or percentage for the total number of the plurality of probing sequences or the plurality of oligonucleotides.

In the present invention, when the reference probing sequence or the reference oligonucleotide is maximally matched with the plurality of probing sequences or the plurality of oligonucleotides by introducing the degenerate base and/or universal base in a predetermined allowable number, the reference probing sequence or a sequence of the reference oligonucleotide into which at least one of the degenerate base and/or the universal base is introduced is selected as a sequence of an oligonucleotide with a maximum target coverage.

The oligonucleotide sequence selected from the reference probing sequence into which the degenerate base and/or universal base is introduced may be used to detect a plurality of target nucleic acid sequences corresponding to a plurality of probing sequences that are maximally matched with the reference probing sequence into which the degenerate base and/or universal base is introduced. The oligonucleotide sequence selected from the reference oligonucleotide sequence into which the degenerate base and/or universal base is introduced may be used to detect a plurality of target nucleic acid sequences corresponding to a plurality of oligonucleotide sequences that are maximally matched with the reference oligonucleotide into which the degenerate base and/or universal base is introduced.

Selecting as the sequence of the oligonucleotide the reference probing sequence or the sequence of the reference oligonucleotide into which at least one of the degenerating base and/or the universal base is introduced may encompass both (i) selecting as the sequence of the oligonucleotide either the reference probing sequence or the sequence of the reference oligonucleotide into which at least one of the degenerate base and/or the universal base is introduced and (ii) selecting as the sequence of the oligonucleotide either a complementary sequence to the reference probing sequence or a complementary sequence to the sequence of the reference oligonucleotide into which at least one of the degenerate base and/or the universal base is introduced.

The term "target coverage" used herein with referring to an oligonucleotide prepared by the present invention refers to a value indicating a proportion of the plurality of target nucleic acid sequences with which the prepared oligonucleotide is specifically hybridized.

Particularly, the term "target coverage" refers to the proportion of the target nucleic acid sequence to the plurality of target nucleic acid sequences with which the prepared oligonucleotide is hybridized with a substantial complementarity (particularly, with perfect complementarity or with perfect match). The target coverage may be expressed as the proportion or percentage.

According to one embodiment of the present invention, the oligonucleotide is a probe and/or a primer. The term used herein "probe" refers to a single-stranded nucleic acid molecule comprising a portion or portions that are complementary to a target nucleic acid sequence. The term "primer" as used herein refers to an oligonucleotide, which is capable of acting as a point of initiation of synthesis when placed under conditions in which synthesis of primer extension product which is complementary to a target nucleic acid sequence is induced, i.e., in the presence of nucleotides and an agent for polymerization, such as DNA polymerase, and at a suitable temperature and pH.

The oligonucleotides prepared in the present invention may have conventional primer and probe structure consisted of sequences that are hybridized with a target nucleic acid sequence. Alternatively, the oligonucleotide prepared in the present invention may have a unique structure. For example, the oligonucleotides prepared in the present invention may have a structure of Scorpion primer, Molecular beacon probe, Sunrise primer, HyBeacon probe, tagging probe, DPO primer or probe (WO 2006/095981), and PTO probe (WO 2012/096523).

The oligonucleotides prepared in the present invention may be a modified oligonucleotide such as a degenerate base-containing oligonucleotide and/or a universal base-containing oligonucleotide, which degenerate bases and/or universal bases are introduced into a conventional primer or probe. The term used herein "conventional primer", "conventional probe", and "conventional oligonucleotide" refer to a common primer, probe, and oligonucleotide into which a degenerate base or non-natural base is not introduced. According to an embodiment, when a degenerate base-containing oligonucleotide or a universal base-containing oligonucleotide is prepared in the present invention, at least 50%, at least 60%, at least 70%, at least 80%, at least 90% or at least 95% of the oligonucleotide are non-modified oligonucleotide. The degenerate base includes the various degenerate bases known in the art as follows: R: A or G; Y: C or T; S: G or C; W: A or T; K: G or T; M: A or C; B: C or G or T; D: A or G or T; H: A or C or T; V: A or C or G;

N: A or C or G or T. The universal base includes the following various universal bases known in the art: deoxyinosine, inosine, 7-deaza-2'-deoxyinosine, 2-aza-2'-deoxyinosine, 2'-OMe inosine, 2'-F inosine, deoxy 3-nitropyrrole, 3-nitropyrrole, 2'-OMe 3-nitropyrrole, 2'-F 3-nitropyrrole, 1-(2'-deoxy-beta-D-ribofuranosyl)-3-nitropyrrole, deoxy 5-nitropyrrole, 5-nitroindole, 2'-OMe 5-nitroindole, 2'-F 5-nitroindole, deoxy 4-nitrobenzimidazole, 4-nitrobenzimidazole, deoxy 4-aminobenzimidazole, 4-aminobenzimidazole, deoxy nebularine, 2'-F nebularine, 2'-F 4-nitrobenzimidazole, PNA-5-introindole, PNA-nebularine, PNA-inosine, PNA-4-nitrobenzimidazole, PNA-3-nitropyrrole, morpholino-5-nitroindole, morpholino-nebularine, morpholino-inosine, morpholino-4-nitrobenzimidazole, morpholino-3-nitropyrrole, phosphoramidate-5-nitroindole, phosphoramidate-nebularine, phosphoramidate-inosine, phosphoramidate-4-nitrobenzimidazole, phosphoramidate-3-nitropyrrole, 2'-O-methoxyethyl inosine, 2'O-methoxyethyl nebularine, 2'-O-methoxyethyl 5-nitroindole, 2'-O-methoxyethyl 4-nitrobenzimidazole, 2'-O-methoxyethyl 3-nitropyrrole, and combinations thereof. More particularly, the universal base is deoxyinosine, inosine, or combinations thereof.

According to one embodiment, the base introduced for a maximum target coverage is a degenerate base. Degenerate oligonucleotides include a plurality of oligonucleotides represented by degenerate oligonucleotides. Unless especially stated otherwise herein, degenerate oligonucleotides refer to a subgroup comprising a plurality of oligonucleotides represented by degenerate oligonucleotides, rather than a single oligonucleotide The oligonucleotides prepared in the present invention may be probes or primers that satisfy at least one of the following additional criteria: (i) a $T_m$ value of 35° C. to 85° C.; (ii) a length of 15-50 nucleotides; (iii) a nucleotide sequence with 30-80% GC content; (iv) ΔG value in which the oligonucleotide forms a hairpin structure is −8.0 kcal/mol or more; (v) when the oligonucleotide forms a homodimer, the ratio of consecutive nucleotides involved in the formation of the homodimer is 65% or less; (vi) when the oligonucleotide forms a heterodimer with another oligonucleotide, the ratio of nucleotides involved in the formation of the heterodimer is 70% or less; and (vii) when the oligonucleotide forms a heterodimer with another oligonucleotide, the ratio of consecutive nucleotides involved in the formation of the heterodimer is 65% or less.

According to one embodiment of the present invention, the method further comprises, between the steps (a) and (b), (a-1) grouping the plurality of probing sequences or the plurality of oligonucleotides according to sequence identity to obtain a plurality of sequence patterns; wherein the step (c) is performed by introducing the degenerate base and/or universal base in a predetermined allowable number into the reference probing sequence or the reference oligonucleotide at the position(s) mismatched between the reference probing sequence or the reference oligonucleotide and the plurality of sequence patterns to be maximally matched with the plurality of sequence patterns, thereby preparing the oligonucleotide with the maximum target coverage.

By grouping the plurality of probing sequences or the plurality of oligonucleotides according to sequence identity to obtain a plurality of sequence patterns, it becomes possible to reduce the comparison number of probing sequences or oligonucleotides for whether to be matched or mismatched with the reference probing sequence or the reference oligonucleotide, thereby reducing a time for providing the oligonucleotide having a maximum target coverage.

The above-mentioned step (c) may be applied to a plurality of sequence patterns of a plurality of probing sequences or a plurality of oligonucleotides.

According to an embodiment of the present invention, the plurality of sequence patterns each has a unique serial number.

According to an embodiment, the reference probing sequence is a probing sequence of a sequence pattern having the largest number of probing sequences grouped into a sequence pattern among the plurality of sequence patterns, and the reference oligonucleotide is an oligonucleotide of a sequence pattern having the largest number of oligonucleotides grouped into a sequence pattern among the plurality of sequence patterns.

One of the features of the present invention is to the application of linear programming as optimization logic, in optimally introducing a degenerate base and/or universal base in a predetermined allowable number into an oligonucleotide used to detect a plurality of target nucleic acid sequences having sequence similarity with a maximum target coverage.

The "linear programming" used in the present invention is an optimization technique that maximizes or minimizes a linear objective function while satisfying a given linear constraint formula (including constraint formula of non-negative number of a variable, a variable≥0). Linear programming uses mathematical models to express problems, and both objective and constraint formulas are linear forms (i.e., linear function).

According to an embodiment of the present invention, the step (c) is performed to achieve the following objective formula 1 together with satisfying the following constraint formulas 1 and 2:

$$\text{Max:} \sum_{i=1}^{r} x_i \qquad \text{Objective formula 1}$$

wherein Max: represents maximization; $x_i$ is a binary variable consisting of a non-selection value ($x_{non\text{-}sel}$) and a selection value ($x_{sel}$) for whether or not the $i^{th}$ probing sequence of the plurality of probing sequences or $i^{th}$ oligonucleotide of the plurality of oligonucleotides is selected; and i is a serial number of probing sequences or oligonucleotides ranging from 1 to r;

$$\sum_{j=1}^{c} d_j \leq D_{Lim} \qquad \text{Constraint formula 1}$$

wherein $d_j$ is a binary variable consisting of a non-introduction value ($d_{non\text{-}int}$) and an introduction value ($d_{int}$) representing whether to introduce the degenerate base and/or universal base at the $j^{th}$ position of the reference probing sequence or the reference oligonucleotide; j is a serial number of positions of a reference probing sequence or a reference oligonucleotide ranging from 1 to c; and $D_{Lim}$ is a limited number of the degenerate base and/or universal base introduced into the reference probing sequence or the reference oligonucleotide;

$$x_i \leq \min\{a_{i,j} + d_j\} \text{ for all } i,j \qquad \text{Constraint formula 2}$$

wherein $x_i$ is a binary variable consisting of a non-selection value ($x_{non\text{-}sel}$) and a selection value ($x_{sel}$) for whether or not the $i^{th}$ probing sequence of the plurality of probing sequences or $i^{th}$ oligonucleotide of the plurality of oligonucleotides is selected; $a_{i,j}$ is a binary constant representing whether the $i^{th}$ probing sequence is matched or mismatched at the $j^{th}$ position with the reference probing sequence or the $i_{th}$ oligonucleotide is matched or mismatched at the $j^{th}$ position with the reference oligonucleotide; $d_j$ is a binary variable consisting of a non-introduction value ($d_{non-int}$) and an introduction value ($d_{int}$) representing whether to introduce the degenerate base and/or universal base at the $j^{th}$ position of the reference probing sequence or the reference oligonucleotide; $a_{i,j}+d_j$ is a binary variable representing whether the reference probing sequence with or without the introduced degenerate base and/or universal base is matched or mismatched at the $j^{th}$ position with the $i^{th}$ probing sequence or the reference oligonucleotide with or without the introduced degenerate base and/or universal base is matched or mismatched at the $j^{th}$ position with the $i^{th}$ oligonucleotide; $\{a_{i,j}+d_j\}$ represents a set including $a_{i,j}+d_j$ as elements; min $\{a_{i,j}+d_j\}$ represents a minimum value among the elements of the set $\{a_{i,j}+d_j\}$; and for all i, j represents application to all positions of all the probing sequences or the oligonucleotides.

The problem to be solved by the linear programming in the present invention is that a limited number of the degenerate base and/or universal base have to be introduced into an oligonucleotide to represent a maximum target coverage.

In order to determine the maximum target coverage, whether to select each of the plurality of probing sequences or the plurality of oligonucleotides for maximally matching with the reference probing sequence or the reference oligonucleotide has to be determined.

Thus, in this invention, $x_i$ is adopted as a binary variable consisting of a non-selection value ($x_{non-sel}$) and a selection value ($x_{sel}$) for whether or not the $i^{th}$ probing sequence of the plurality of probing sequences or $i^{th}$ oligonucleotide of the plurality of oligonucleotides is selected. Here, i is a serial number of probing sequences or oligonucleotides ranging from 1 to r, the r is the serial number of the last probing sequence or oligonucleotide.

Since $x_i$ is a binary variable consisting of a non-selection value ($x_{non-sel}$) and a selection value ($x_{sel}$) for whether or not the $i^{th}$ probing sequence of the plurality of probing sequences or $i^{th}$ oligonucleotide of the plurality of oligonucleotides is selected, when the $i^{th}$ probing sequence or $i^{th}$ oligonucleotide is not selected, it is indicated as the non-selection value ($x_{non-sel}$), and when the $i^{th}$ probing sequence or $i^{th}$ oligonucleotide is selected, it is indicated as the selection value ($x_{sel}$). Particularly, the non-selection value ($x_{non-sel}$) is 0 and the selection value ($x_{sel}$) is a value other than 0. More particularly, the non-selection value ($x_{non-sel}$) and the selection value ($x_{sel}$) of $x_i$ are 0 and 1, respectively.

Because a limited number of the degenerate base and/or universal base have to be introduced into an oligonucleotide, whether to introduce the degenerate base and/or universal base at which position(s) of the reference probing sequence or the reference oligonucleotide has to be determined. Thus, $d_j$ is adopted as a binary variable consisting of a non-introduction value ($d_{non-int}$) and an introduction value ($d_{int}$) representing whether to introduce the degenerate base and/or universal base at the $j^{th}$ position of the reference probing sequence or the reference oligonucleotide. Here, j is a serial number of positions of a reference probing sequence or a reference oligonucleotide ranging from 1 to c, and the c is the serial number of the last position in the reference probing sequence or the reference oligonucleotide.

c is not particularly limited and may be, for example, an integer of 10-100, 10-80, 10-50, 10-40, 10-30, 15-100, 15-80, 15-50, 15-40, 15-30, 20-100, 20-80, 20-50, 20-40, 20-30, 25-100, 25-80, 25-50, 25-40, 25-30, 30-100, 30-80, 30-50, 30-40, 35-100, 35-80, 35-50 or 35-40.

Since $d_j$ is a binary variable representing whether to introduce the degenerate base and/or universal base at the $j^{th}$ position of the reference probing sequence or the reference oligonucleotide, when the degenerate base and/or the universal base is not introduced at the $j^{th}$ position of the reference probing sequence or the reference oligonucleotide, it is indicated as the non-introduction value ($d_{non-int}$), and when the degenerate base and/or the universal base is introduced at the $j^{th}$ position of the reference probing sequence or the reference oligonucleotide, it is indicated as the introduction value ($d_{int}$). Particularly, the non-introduction value ($d_{non-int}$) is 0 and the introduction value ($d_{int}$) is a value other than 0. More particularly, the non-introduction value ($d_{non-int}$) and the introduction value ($d_{int}$) of $d_j$ are 0 and 1, respectively.

Since the oligonucleotide prepared in the present invention has to have the maximum target coverage, the number of the plurality of the probing sequences or the plurality of oligonucleotides matched with the reference probing sequence or the reference oligonucleotide into which the degenerate base and/or universal base is introduced has to be as much as possible. Therefore, the sum of the selection value and the non-selection value for the plurality of probing sequences or the plurality of oligonucleotides becomes an objective function, and the objective function has to be maximized. Therefore, the objective formula in the present invention may be expressed as the objective formula 1.

In addition, in the present invention, by introducing a limited number of the degenerate base and/or universal base into the reference probing sequence or the reference oligonucleotide, the reference probing sequence or the reference oligonucleotide needs to be maximally matched with a plurality of probing sequences or a plurality of oligonucleotides. That is, a limited number of the degenerate base and/or universal base have to be used for the maximum matching or maximum target coverage. Therefore, in the present invention, the constraint formula 1 is set according to this constraint condition.

In the constraint formula 1, $D_{Lim}$ is a limited number of the degenerate base and/or universal base introduced into the reference probing sequence or the reference oligonucleotide.

The limited number of the degenerate base and/or universal base introduced in the present invention is particularly 7, 5, 4 or 3.

In the optimization logic of the present invention, the degenerate base and/or the universal base is introduced into the reference probing sequence or the reference oligonucleotide to be maximally matched with the plurality of probing sequences or the plurality of oligonucleotides. Therefore, required is a constraint formula related to whether to be matched after introducing the degenerate base and/or the universal base into the reference probing sequence or the reference oligonucleotide and whether to select the $i^{th}$ probing sequence among the plurality of probing sequences or the $i^{th}$ oligonucleotide among the plurality of oligonucleotides. For this reason, the constraint formula 2 is set.

A matching or mismatching value representing whether to be matched or mismatched between the reference probing sequence or reference oligonucleotide into which the degenerate base and/or universal base is not introduced and a plurality of probing sequences or a plurality of oligonucleotides is not a variable but a constant. For this reason, $a_{i,j}$ is adopted, which is a binary constant representing whether or not the $i^{th}$ probing sequence is matched or mismatched at the $j^{th}$ position with the reference probing sequence or $i^{th}$ oligonucleotide is matched or mismatched at the $j^{th}$ position with the reference oligonucleotide.

Particularly, when the $j^{th}$ position of the reference probing sequence before introduction of the degenerate base and/or the universal base is matched with the $j^{th}$ position of the $i^{th}$ probing sequence or the $j^{th}$ position of the reference oligonucleotide before introduction of the degenerate bases and/or the universal bases is matched with the $j^{th}$ position of the $i^{th}$ oligonucleotide, $a_{i,j}$ has a matching value; otherwise, $a_{i,j}$ has a mismatching value. Particularly, the mismatching value is 0 and the matching value is a value other than 0. More particularly, the mismatching value and the matching value of $a_{i,j}$ are 0 and 1, respectively.

In addition, $a_{i,j}+d_j$ is selected as a binary variable representing whether the reference probing sequence with or without the introduced degenerate base and/or universal base is matched or mismatched at the $j^{th}$ position with the $i^{th}$ probing sequence or the reference oligonucleotide with or without the introduced degenerate base and/or universal base is matched or mismatched at the $j^{th}$ position with the $i^{th}$ oligonucleotide.

Particularly, when the degenerate base and/or the universal base is introduced at the $j^{th}$ position of the reference probing sequence or the reference oligonucleotide, are not introduced at the $j+1^{th}$ position, and the $j^{th}$ position of the reference probing sequence is matched with the $j^{th}$ position of the $i^{th}$ probing sequence or the $j^{th}$ position of the reference oligonucleotide is matched with the $j^{th}$ position of the $i^{th}$ oligonucleotide, $a_{i,j}+d_j$ has the matching value; otherwise, $a_{i,j}+d_j$ has the mismatching value. When the $j+1^{th}$ position of the reference probing sequence is matched with the $j+1^{th}$ position of the $i^{th}$ probing sequence or the $j+1^{th}$ position of the reference oligonucleotide is matched with the $j+1^{th}$ position of the $i^{th}$ oligonucleotide, $a_{i,j+1}+d_{j+1}$ has the matching value; otherwise, $a_{i,j+i}+d_{j+1}$ has the mismatching value. Particularly, the mismatching value is 0 and the matching value is a value other than 0. More particularly, the mismatching value is 0 and the matching value is 1 or 2.

Here, the minimum value of the set $\{a_{i,j}+d_j\}$ having the matching value and/or mismatching value of $a_{i,j}+d_j$ as elements is larger than or equal to $x_i$, a binary variable having a non-selection value ($x_{non-sel}$) and a selection value ($x_{sel}$) for whether or not the $i^{th}$ probing sequence of the plurality of probing sequences or $i^{th}$ oligonucleotide of the plurality of oligonucleotides is selected. For example, when the minimum value of the set $\{a_{i,j}+d_j\}$ having the matching value and/or mismatching value of $a_{i,j}+d_j$ as elements has a mismatching value, the minimum value of $\{a_{i,j}+d_j\}$ has to be equal to $x_i$ having the non-selection value ($x_{non-sel}$), and the minimum value of the set $\{a_{i,j}+d_j\}$ having the matching value and/or mismatching value of $a_{i,j}+d_j$ as elements has a matching value, the minimum value of $\{a_{i,j}+d\}$ must be equal to or larger than $x_i$ having the selection value ($x_{sel}$).

In other words, the value (matching value) of $a_{i,j}+d_j$ at the $j^{th}$ position of the $i^{th}$ probing sequence or $i^{th}$ oligonucleotide matched for the reference probe sequence or the reference oligonucleotide into which the degenerate base and/or universal base is introduced is equal to or greater than the selected value ($x_{sel}$); the value (matching value) of $a_{i,j}+d_j$ at the $j^{th}$ position of the $i^{th}$ probing sequence or $i^{th}$ oligonucleotide matched for the reference probe sequence or the reference oligonucleotide into which the degenerate base and/or universal base is not introduced is equal to or greater than the selected value ($x_{sel}$); and the value (mismatching value) of $a_{i,j}+d_j$ at the $j^{th}$ position of the $i^{th}$ probing sequence or $i^{th}$ oligonucleotide mismatched for the reference probe sequence or the reference oligonucleotide into which the degenerate base and/or universal base is not introduced is equal to or greater than the non-selected value ($x_{non-sel}$) and is smaller than the selected value ($x_{sel}$).

The constraint formula 2 is set to satisfy these constraint conditions.

Where the method is performed to achieve the objective formula 1 together with satisfying the constraint formulas 1 and 2, the decision variables $d_j$ and $x_i$ values may be obtained as the optimal solutions, and the maximum target coverage of the oligonucleotide prepared by the present invention may be obtained by dividing the sum of $x_i$ values by the total number of the plurality of probing sequences or the plurality of oligonucleotides.

According to an embodiment of the present invention, the method selects the target nucleic acid sequences to be detected and provides an oligonucleotide which at least one of the degenerate base and/or the universal bases in the predetermined allowable number is introduced into and the selected target nucleic acid sequence are hybridized with.

The target nucleic add sequences to be detected may be selected through the $x_i$ value, which is the optimal solution obtained by carrying out to achieve the objective formula 1 together with satisfying the constraint formulas 1 and 2, and the oligonucleotide into which the degenerate base and/or the universal base is introduced within the predetermined allowable number to be hybridized with the selected target nucleic acid sequence may be prepared through the optimal solution, the $d_j$ value.

It is noteworthy that not only an oligonucleotide into which at least one of degenerate base and/or universal base is optimally introduced but also target nucleic acid sequences to be targeted, i.e., covered by the oligonucleotide may be selected through one objective formula.

According to one embodiment, wherein the constraint formula 1 is the following constraint formulas 1-1 and 1-2:

$$\sum_{j=1}^{b} d_j \leq D_{Lim1} \quad \text{Constraint formula 1-1}$$

$$\sum_{j=b+1}^{c} d_j \leq D_{Lim2} \quad \text{Constraint formula 1-2}$$

wherein $d_j$ is a binary variable consisting of a non-introduction value ($d_{non-int}$) and an introduction value ($d_{int}$) representing whether to introduce the degenerate base and/or universal base at the $j^{th}$ position of the reference probing sequence or the reference oligonucleotide; j is a serial number of positions of a reference probing sequence or a reference oligonucleotide ranging from 1 to c; the reference probing sequence or the reference oligonucleotide comprises the first portion ranging from 1 to b and the second portion ranging from b+1 to c; and $D_{Lim1}$ and $D_{Lim2}$ is a limited number of the degenerate base and/or universal base introduced into the first and second portions of the reference probing sequence or the reference oligonucleotide, respectively.

By modifying the constraint formula 1 to the constraint formulas 1-1 and 1-2, the step (c) in the present invention may be performed to achieve the following objective formula 1 together with satisfying the constraint formulas 1-1, 1-2 and 2.

In the present invention, the linear programming may be applied to two different portions of one reference probing sequence or reference oligonucleotide independently or simultaneously, and particularly may be applied simultaneously.

Since the descriptions for a binary variable $d_j$, a serial number of positions j and the last serial number c in the constraint formula 1-1 and 1-2 is identical to those of the constraint formula 1, the common descriptions between them are omitted in order to avoid undue redundancy leading to the complexity of this specification.

The reference probing sequence or the reference oligonucleotide comprises the first portion ranging from 1 to band the second portion ranging from b+1 to c.

b is the serial number of the last position of the first portion, b+1 is the serial number of the first position of the second portion, and c is the serial number of the last position of the second portion.

The lengths of the first portion and the second portion may be the same or different. Particularly, the first portion may be longer than the second portion.

b is not particularly limited and may be, for example, an integer of 15-40, 15-30 or 20-25.

$D_{Lim1}$ and $D_{Lim2}$ is a limited number of the degenerate base and/or universal base introduced into the first and second portions of the reference probing sequence or the reference oligonucleotide, respectively.

$D_{Lim1}$ and $D_{Lim2}$ may be equal to or different from each other, or $D_{Lim1}$ may be larger than $D_{lim2}$. Alternatively, the $D_{Lim}$ of the constraint formula 1 may be equal to or different from the sum of $D_{Lim1}$ and $D_{Lim2}$.

The limited number of the degenerate base and/or universal base introduced into the first portion of the reference probing sequence or the reference oligonucleotide, $D_{Lim1}$ is particularly 6, 4, 3 or 2. The limited number of the degenerate base and/or universal base introduced into the second portion of the reference probing sequence or the reference oligonucleotide, $D_{Lim2}$ is particularly 5, 3, 2 or 1.

According to one embodiment of the present invention, wherein the constraint formula 1 is the following constraint formulas 1-1 and 1-3:

$$\sum_{j=1}^{b} d_j \leq D_{Lim1} \quad \text{Constraint formula 1-1}$$

$$\sum_{j=b+n}^{c} d_j \leq D_{Lim3} \quad \text{Constraint formula 1-3}$$

wherein $d_j$ is a binary variable consisting of a non-introduction value ($d_{non-int}$) and an introduction value ($d_{int}$) representing whether to introduce the degenerate base and/or universal base at the $j^{th}$ position of the reference probing sequence or the reference oligonucleotide; j is a serial number of positions of a reference probing sequence or a reference oligonucleotide ranging from 1 to c; the reference probing sequence or the reference oligonucleotide comprises the first portion ranging from 1 to b, a second portion ranging from b+1 to b+(n−1), and the third portion ranging from b+n to c; n is an integer of 2 to 10; $D_{Lim1}$ and $D_{Lim3}$ is a limited number of the degenerate base and/or universal base introduced into the first and third portions of the reference probing sequence or the reference oligonucleotide, respectively; and the second portion represents a separation portion comprising universal bases, non-natural bases or non-complementary bases to bases of the second portion.

By modifying the constraint formula 1 to the constraint formulas 1-1 and 1-3, the step (c) in the present invention may be performed to achieve the following objective formula 1 together with satisfying the constraint formulas 1-1, 1-3 and 2.

In the present invention, the linear programming may be applied independently or simultaneously to two different portions other than the separation portion among three different portions within one reference probing sequence or reference oligonucleotide, and particularly, it may be applied to two different portions simultaneously.

Since the descriptions for a binary variable $d_j$, a serial number of positions j; and the last serial number of the first portion b in the constraint formula 1-1 and 1-3 is identical to those of the constraint formula 1-1 and 1-2, the common descriptions between them are omitted in order to avoid undue redundancy leading to the complexity of this specification.

The reference probing sequence or the reference oligonucleotide comprises the first portion ranging from 1 to b, a second portion ranging from b+1 to b+(n−1), and the third portion ranging from b+n to c.

b is the serial number of the last position of the first portion, b+1 is the serial number of the first position of the second portion, b+(n−1) is the serial number of the last position of the second portion, b+n is the serial number of the first position of the third portion, and c is the serial number of the last position of the third portion.

In addition, n is an integer of 2-10, 3-10, 4-8 or 5-7.

One reference probing sequence or reference oligonucleotide is separated into the first portion and the third portion by the second portion as a separation portion and the degenerate base and/or universal base in a predetermined allowable number is introduced into the first portion and the third portion independently or simultaneously.

The second portion represents a separation portion comprising universal bases, non-natural bases or non-complementary base to bases of the second portion.

The second portion as the separation portion comprises non-contiguous or contiguous nucleotides having universal bases, non-natural bases or non-complementary bases to bases of the second portion.

The number of universal bases, non-natural bases, or non-complementary base to bases of the second portion included in the second portion as the separation portion is 2-9, 3-9, 4-8 or 5-7.

The above description of the universal base is applied to the universal base included in the second portion.

The term used herein "non-natural base" refers to derivatives of natural bases such as adenine (A), guanine (G), thymine (T), cytosine (C) and uracil (U), which are capable of forming hydrogen-bonding base pairs. The term used herein "non-natural base" includes bases having different base pairing patterns from natural bases as mother compounds, as described, for example, in U.S. Pat. Nos. 5,432,272, 5,965,364, 6,001,983, and 6,037,120. Specific examples of non-natural bases include K, X, H, J, M, N, iso-C, iso-G, iso-dC and iso-dG.

The non-complementary bases to bases of the second portion means, for example, that when the bases of positions j=b+1 and b+2 in the second portion are A and G respectively, they include C or G and A or T, respectively.

It is critical that the separation portion in the oligonucleotide prepared by this invention has the lowest $T_m$, in the three portions, in order that the separation portion forms a non base-pairing bubble structure under conditions that the first and second portions are annealed to the template nucleic acid, enabling one of the first and second portions to separate from the other portion in terms of annealing specificity to the template nucleic acid, whereby the annealing specificity of the oligonucleotide is determined dually by the first and second portions such that the overall annealing specificity of the oligonucleotide is considerably enhanced.

The lengths of the first portion and the third portion may be the same or different. Particularly, the first portion may be longer than the third portion.

$D_{Lim1}$ and $D_{Lim3}$ is a limited number of the degenerate base and/or universal base introduced into the first and third portions of the reference probing sequence or the reference oligonucleotide, respectively.

$D_{Lim1}$ and $D_{Lim3}$ may be equal to or different from each other, or $D_{Lim1}$ may be larger than $D_{Lim3}$. Alternatively, the $D_{Lim}$ of the constraint formula 1 may be equal to or different from the sum of $D_{Lim1}$ and $D_{Lim3}$.

The limited number of the degenerate base and/or universal base introduced into the first portion of the reference probing sequence or the reference oligonucleotide, $D_{Lim1}$ is particularly 6, 4, 3 or 2. The limited number of the degenerate base and/or universal base introduced into the third portion of the reference probing sequence or the reference oligonucleotide, $D_{Lim3}$ is particularly 5, 3, 2 or 1.

The term used herein "coverage" means that an oligonucleotide (a primer or a probe) is sufficiently complementary to be selectively hybridized with a target nucleic acid sequence under the designated annealing conditions or stringent conditions, encompassing the terms "substantially complementary" and "perfectly complementary", particularly perfectly complementary.

The term used herein "hybridization" means forming a double-stranded nucleic acid from a complementary single-stranded nucleic acid. An oligonucleotide to be hybridized with a target nucleic acid sequence includes not only sequence that is perfectly complementary to a target nucleic acid sequence but also sequence that is enough to be specifically hybridized with a target nucleic acid sequence under certain stringent conditions. For example, an oligonucleotide may comprise one or more non-complementary nucleotides (i.e., mismatches) to a target nucleic acid sequence, as long as its specificity is not impaired. Therefore, in the present invention, an oligonucleotide may comprise a partially complementary and a perfectly complementary sequence to a target nucleic acid sequence, and particularly includes a perfectly complementary sequence (or a matching sequence).

When the method further comprises, between the steps (a) and (b), (a-1) grouping the plurality of probing sequences or the plurality of oligonucleotides according to sequence identity to obtain a plurality of sequence patterns, the step (c) of the present invention may be carried out as follows.

According to an embodiment, the step (c) is performed to achieve the following objective formula 2 together with satisfying the following constraint formulas 3 and 4:

$$\text{Max:} \sum_{i=1}^{r} p_i x_i \qquad \text{Objective formula 2}$$

wherein Max: represents maximization; $p_i$ is the number of probing sequences belonging to the $i^{th}$ sequence pattern of probing sequences or the number of oligonucleotides belonging to the $i^{th}$ sequence pattern of oligonucleotides; $x_i$ is a binary variable consisting of a non-selection value ($x_{non-sel}$) and a selection value ($x_{sel}$) for whether or not the $i^{th}$ sequence pattern of probing sequences or $i^{th}$ sequence pattern of oligonucleotides is selected; and i is a serial number of sequence patterns of probing sequences or oligonucleotides ranging from 1 to r;

$$\sum_{j=1}^{c} d_j \leq D_{Lim} \qquad \text{Constraint formula 3}$$

wherein $d_j$ is a binary variable consisting of a non-introduction value ($d_{non-int}$) and an introduction value ($d_{int}$) representing whether to introduce the degenerate base and/or universal base at the $j^{th}$ position of the reference probing sequence or the reference oligonucleotide; j is a serial number of positions of the reference probing sequence or the reference oligonucleotide ranging from 1 to c; and $D_{Lim}$ is a limited number of the degenerate base and/or universal base introduced into the reference probing sequence or the reference oligonucleotide;

$$x_i \leq \min\{a_{i,j}+d_j\} \text{ for all } i,j \qquad \text{Constraint formula 4}$$

wherein $x_i$ is a binary variable consisting of a non-selection value ($x_{non-sel}$) and a selection value ($x_{sel}$) for whether or not the $i^{th}$ sequence pattern of probing sequences or $i^{th}$ sequence pattern of oligonucleotides is selected; $a_{i,j}$ is a binary constant representing whether a probing sequence belonging to the $j^{th}$ sequence pattern of probing sequences is matched or mismatched at the $j^{th}$ position with the reference probing sequence or an oligonucleotide belonging to the $i^{th}$ sequence pattern of oligonucleotides is matched or mismatched at the $j^{th}$ position with the reference oligonucleotide; $d_j$ is a binary variable consisting of a non-introduction value ($d_{non-int}$) and an introduction value ($d_{int}$) representing whether to introduce the degenerate base and/or universal base at the $j^{th}$ position of the reference probing sequence or the reference oligonucleotide; $a_{i,j}+d_j$ is a binary variable representing whether the reference probing sequence with or without the introduced degenerate base and/or universal base is matched or mismatched at the $j^{th}$ position with a probing sequence belonging to the $i^{th}$ sequence pattern of probing sequences or the reference oligonucleotide with or without the introduced degenerate base and/or universal base is matched or mismatched at the $j^{th}$ position with the oligonucleotide belonging to the $i^{th}$ sequence pattern of oligonucleotides; $\{a_{i,j}+d_j\}$ represents a set including $a_{i,j}+d_j$ as elements; min $\{a_{i,j}+d_j\}$ represents a minimum value among the elements of the set $\{a_{i,j}+d\}$; and for all i, j represents application to all positions of all the probing sequences or the oligonucleotides.

In order to apply the objective formula 1, the constraint formulas 1 and 2 to a plurality of sequence patterns of a plurality of probing sequences or a plurality of oligonucleotides, the objective formula 1, the constraint formulas 1 and 2 are reconstructed into the objective formula 2, the constraint formulas 3 and 4 for a plurality of sequence patterns. Therefore, the descriptions for the plurality of probing sequences or the plurality of oligonucleotides in the objective formula 1, the constraint formulas 1 and 2 are represented by the descriptions for the plurality of sequence patterns in the objective formula 2, the constraint formulas 3 and 4. In addition, the common descriptions between the objective formula 1, the constraint formulas 1 and 2, and the objective formula 2, the constraint formulas 3 and 4 are omitted in order to avoid undue redundancy leading to the complexity of this specification.

In the objective formula 2, $p_i$ is the number of probing sequences belonging to the $i^{th}$ sequence pattern of probing sequences or the number of oligonucleotides belonging to the $i^{th}$ sequence pattern of oligonucleotides.

Where the method is carried out to achieve the objective formula 2 together with satisfying the constraint formulas 3 and 4, the decision variables $d_j$ and $x_i$ may be obtained as optimal solutions.

If a non-selection value ($x_{non-sel}$) or a selection value ($x_{sel}$) of the $i^{th}$ sequence pattern of probing sequences or the $i^{th}$ sequence pattern of oligonucleotides is obtained as a solution, the number of target nucleic acid sequences detected by the oligonucleotide prepared by the present invention may be obtained by multiplying $x_i$ of each sequence pattern by the number $p_i$ of probing sequences or oligonucleotides belonging to each sequence pattern and summing the product of $p_i$ and $x_i$ to all the sequence patterns. In addition, the maximum target coverage of the oligonucleotide prepared by the present invention may be determined by dividing the number of the target nucleic acid sequences to be detected by the total number of target nucleic acid sequences.

According to one embodiment, wherein the constraint formula 3 is the following constraint formulas 3-1 and 3-2:

$$\sum_{j=1}^{b} d_j \leq D_{Lim1} \quad \text{Constraint formula 3-1}$$

$$\sum_{j=b+1}^{c} d_j \leq D_{Lim2} \quad \text{Constraint formula 3-2}$$

wherein $d_j$ is a binary variable consisting of a non-introduction value ($d_{non-int}$) and an introduction value ($d_{int}$) representing whether to introduce the degenerate base and/or universal base at the $j^{th}$ position of the reference probing sequence or the reference oligonucleotide; j is a serial number of positions of a reference probing sequence or a reference oligonucleotide ranging from 1 to c; the reference probing sequence or the reference oligonucleotide comprises the first portion ranging from 1 to b and the second portion ranging from b+1 to c; and $D_{Lim1}$ and $D_{Lim2}$ is a limited number of the degenerate base and/or universal base introduced into the first and second portions of the reference probing sequence or the reference oligonucleotide, respectively.

According to one embodiment of the present invention, wherein the constraint formula 3 is the following constraint formulas 3-1 and 3-3:

$$\sum_{j=1}^{b} d_j \leq D_{Lim1} \quad \text{Constraint formula 3-1}$$

$$\sum_{j=b+n}^{c} d_j \leq D_{Lim3} \quad \text{Constraint formula 3-3}$$

wherein $d_j$ is a binary variable consisting of a non-introduction value ($d_{non-int}$) and an introduction value ($d_{int}$) representing whether to introduce the degenerate base and/or universal base at the $j^{th}$ position of the reference probing sequence or the reference oligonucleotide; j is a serial number of positions of a reference probing sequence or a reference oligonucleotide ranging from 1 to c; the reference probing sequence or the reference oligonucleotide comprises the first portion ranging from 1 to b, a second portion ranging from b+1 to b+(n−1), and the third portion ranging from b+n to c; n is an integer of 2 to 10; $D_{Lim1}$ and $D_{Lim3}$ is a limited number of the degenerate base and/or universal base introduced into the first and third portions of the reference probing sequence or the reference oligonucleotide, respectively; and the second portion represents a separation portion comprising universal bases, non-natural bases or non-complementary base to bases of the second portion.

Since the descriptions of the constraint formula 1-1 to 1-3 are identical to those of the constraint formula 3-1 to 3-3, the common descriptions between them are omitted in order to avoid undue redundancy leading to the complexity of this specification. 2

The method of the present invention is particularly useful when an oligonucleotide is designed to detect a plurality of pathogens with genetic diversity such as virus or to screen bacteria genus (e.g., *Campylobacter, Salmonella, Shigella, Vibrio, Aeromonas*).

II. Determination of a Probing Region in a Plurality of Target Nucleic Acid Sequences In the second aspect of this invention, there is provided a method for determining a probing region in a plurality of target nucleic acid sequences having sequence similarity, comprising: (a) selecting one candidate probing region in a plurality of target nucleic acid sequences and providing sequences in the candidate probing region as a plurality of probing sequences; (b) introducing a degenerate base and/or universal base in a predetermined allowable number into the plurality of probing sequences at a position(s) mismatched between the plurality of probing sequences such that the plurality of probing sequences are maximally matched with each other; and (c) determining the candidate probing region as a probing region for detecting all or a part of the plurality of target nucleic acid sequences when the maximum matching is not less than a predetermined coverage.

A probing region refers to a conserved region that comprises sequences conservatively maintained between different organisms, i.e., a conserved sequence as a portion with which a primer or a probe is hybridized. A conserved region which is a biologically very meaningful portion represents a portion where sequences are similar or identical in different nucleic acid molecules between different organisms from each other. The conserved region is used as a very important indicator for phylogenetic studies and is also used as a probing portion when different organisms are detected in a multiplex manner.

According to the present invention, sequences conservatively maintained between different organisms may be determined in a unique manner, and the conserved region comprising these conserved sequences may be used as the portion (i.e., probing region) with which a primer or a probe is hybridized.

The present invention is described as a method for determining a probing region, but this may also be expressed as a method of determining a conserved region. Where the degenerate base and/or universal base in a predetermined allowable number is introduced into the plurality of probing sequences at a position(s) mismatched between the plurality of probing sequences in accordance with the invention described above such that the plurality of probing sequences are maximally matched with each other and the candidate probing region may be presented as a probing region when the maximum matching is not less than a predetermined coverage,.

Since the second method of the present invention is based on the first method of the present invention described above, the common descriptions between them are omitted in order to avoid undue redundancy leading to the complexity of this specification.

Figure 3:
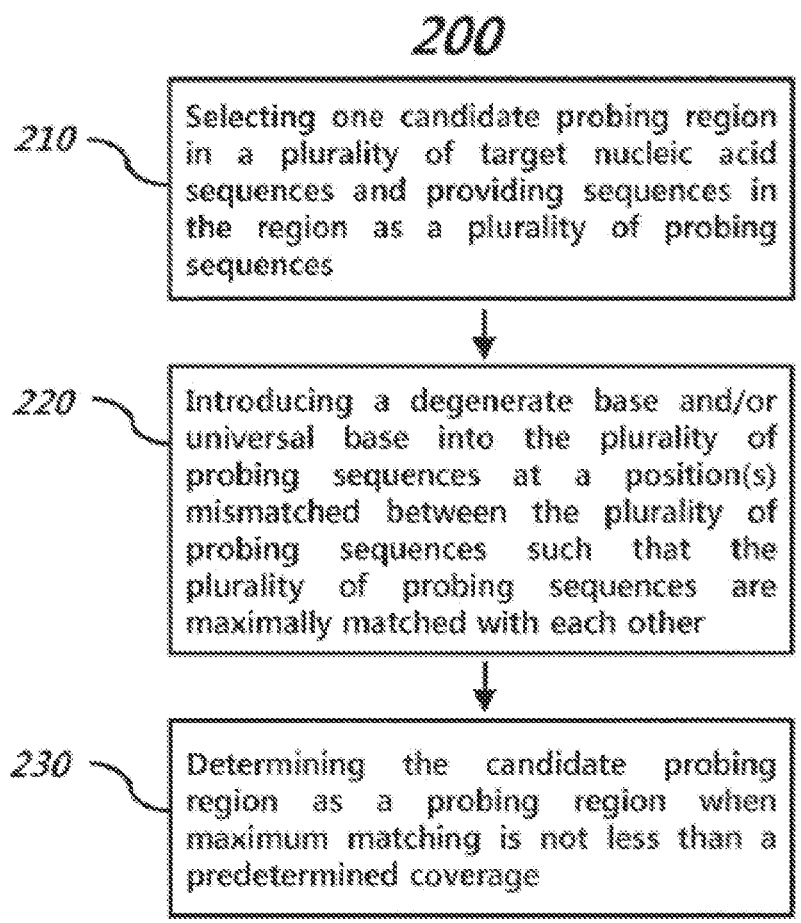
FIG. 3 is a flow diagram showing a process of determining a probing region in a plurality of target nucleic acid sequences with sequence similarity according to an embodiment of the present invention.

FIG. 3 is a flow diagram of the procedures for performing the invention in accordance with an embodiment of the invention. The method of the present invention will be described with reference to FIG. 3:

Step (a): Providing a Plurality of Probing Sequences (210)

First, one candidate probing region is selected in a plurality of target nucleic acid sequences and sequences in the candidate probing region are provided as a plurality of probing sequences.

According to an embodiment, a plurality of target nucleic acid sequences are aligned prior to the step (a).

Since the descriptions of the target nucleic acid sequence and alignment in the step (a) of the second method of the present invention is identical to those of the first method of the present invention, the common descriptions between them are omitted in order to avoid undue redundancy leading to the complexity of this specification.

The plurality of probing sequences provided in the step (a) of the present invention are a comparison reference and subject for determining whether to be mismatched in step (b), and are an introduction subject in introducing degenerate bases and/or universal bases for their maximum matches.

According to an embodiment of the present invention, the plurality of probing sequences each has a unique serial number.

According to an embodiment, the step (a) is performed by selecting at least two candidate probing regions being at different locations in alignment of the plurality of target nucleic acid sequences, and providing in each of the at least two candidate probing regions as a plurality of probing sequences.

Step (b): Introducing a Degenerate Base and/or Universal Base Such that the Plurality of Probing Sequences are Maximally Matched with Each Other (220)

Then, a degenerate base and/or universal base in a predetermined allowable number is introduced into the plurality of probing sequences at a position(s) mismatched between the plurality of probing sequences such that the plurality of probing sequences are maximally matched with each other.

Unlike the first method of the present invention described above, the step (b) of the second method of the present invention may be performed without providing a reference probing sequence as a reference for determining whether to be matched. In the step (b) of the second method of the present invention for determining the probing region, the plurality of probing sequences are not only a comparison subject but also an introduction subject introducing the degenerate base and/or universal base. For example, in probing sequences ranging from 1 to 3, when the base at position 3 of the probing sequences 1, 2 and 3 is "A", "C" and "G", respectively, the degenerate base V (A or C or G) may be introduced at position 3 for the maximum matching.

The term "maximum matching" used herein with referring to the introduction of the degenerate base and/or universal base means that the same sequences are included as much as possible in a plurality of probing sequences by introducing the degenerate base and/or universal base and the maximum matching may be expressed as a proportion or percentage with regard to the total number of the plurality of probing sequences.

Since the description of the degenerate base and/or universal base in the step (b) of the second method of the present invention is the same as that of the first method of the present invention, the common descriptions between them are omitted in order to avoid undue redundancy leading to the complexity of this specification.

According to an embodiment of the present invention, the step (b) is performed by selecting one of the plurality of probing sequences as a reference probing sequence and introducing the degenerate base and/or universal base in a predetermined allowable number into the reference probing sequence at a position(s) mismatched between the reference probing sequence and the plurality of probing sequences to be maximally matched with the plurality of probing sequences.

In step (b) of the present invention, as a comparison reference for determining whether to be mismatched and an introduction subject introducing the degenerate base and/or universal base, the reference probing sequence may be selected from a plurality of probing sequences.

For example, in probing sequences ranging from 1 to 3, when the base at position 3 of the probing sequences 1, 2 and 3 is "A", "C" and "G", respectively, the probing sequence 1 is selected as the reference probing sequence, compared with the probing sequences 2 and 3 and then the degenerate base V (A or C or G) may be introduced at position 3 of the reference probing sequence for the maximum matching.

According to an embodiment, the reference probing sequence is a probing sequence having the largest number of identical sequences among the plurality of probing sequences.

According to an embodiment of this invention, the step (b) is performed by introducing the degenerate base and/or universal base in a predetermined allowable number into the plurality of probing sequences at a position(s) mismatched with each other in the plurality of sequence patterns for each of the at least two candidate probing regions such that the plurality of sequence patterns are maximally matched with each other.

Step (c): Determining a probing region (230)

Afterward, when the maximum matching is not less than a predetermined coverage, the candidate probing region is determined as a probing region for detecting all or a part of the plurality of target nucleic acid sequences.

The term "coverage" used herein with referring to the probing region in the present invention means the proportion of perfectly matched sequences in the plurality of probing sequences into which the degenerate base and/or universal base is introduced. The coverage may be expressed by the proportion or percentage.

The coverage is 20% or more, 40% or more, 60% or more, 80% or more, 90% or more, or 100% for the total number of the plurality of probing sequences.

Where the plurality of probing sequences are maximally matched with each other by introducing the degenerate base and/or universal base and the maximum matching is not less than a predetermined coverage, the candidate probing region to which the plurality of probing sequences belong is determined as the probing region for detecting all or a part of the plurality of target nucleic acid sequences.

According to an embodiment, the step (c) is performed by determining as a probing region for detecting all or a part of the plurality of target nucleic acid sequences, among the at least two candidate probing regions, (i) a candidate probing region in which the maximum matching is not less than the predetermined coverage and the highest maximum matching is shown, (ii) a candidate probing region in which the maximum matching is not less than the predetermined coverage and a minimum number of the degenerate base and/or universal base is introduced for the maximum matching, or (iii) a candidate probing region in which the maximum matching is not less than the predetermined coverage, the highest maximum matching is shown and a minimum number of the degenerate base and/or universal base is introduced for the maximum matching.

For example, candidate probing regions 1-3 being at different locations are selected in the alignment of the plurality of target nucleic acid sequences, the predetermined coverage is 90% or more, and three or less degenerate bases are introduced into the plurality of probing sequences for each of the candidate probing regions 1 to 3 at a position(s) mismatched between the plurality of probing sequences. As a result, the candidate probing region 1 represents a maximum matching rate of 95% by introducing one degenerate base, the candidate probing region 2 a maximum matching rate of 99% by introducing two degenerate base, and the candidate probing region 3 a maximum matching rate 99% by introducing three degenerate base.

According to criterion (i) for determining the probing region, the candidate probing regions 2 and 3 which have not less than 90% coverage and the greatest maximum matching rate of 99% may be determined as the probing regions, since the degenerate base may be introduced within the number of three. Alternatively, according to criterion (ii), although the maximum matching rate is not less than the predetermined coverage in all the candidate probing regions 1 to 3, the candidate probing region 1 may be determined as the probing region because of using the smallest number of degenerate bases, i.e., one degenerate base, for a maximum matching. Alternatively, according to criterion (iii), as the probing region, the candidate probing region 2 may be determined in which the maximum matching rate is not less than the predetermined coverage, the maximum matching is the largest, and the smallest number of degenerate bases is introduced for the largest maximum matching.

According to an embodiment of the present invention, the method further comprises, between the steps (a) and (b), (a-1) grouping the plurality of probing sequences according to sequence identity to obtain a plurality of sequence patterns; wherein the step (b) is performed by introducing the degenerate base and/or universal base in a predetermined allowable number into the plurality of probing sequences at a position(s) mismatched with each other in the plurality of sequence patterns such that the plurality of sequence patterns are maximally matched with each other; and the step (c) is performed by determining the candidate probing region to which the sequence pattern belongs as a probing region for detecting all or a part of the plurality of target nucleic acid sequences when the maximum matching is not less than a predetermined coverage.

According to an embodiment, the method further comprises, between the steps (a) and (b), (a-1) grouping the plurality of probing sequences of each of the at least two candidate probing regions according to sequence identity to obtain a plurality of sequence patterns; wherein the step (b) is performed by introducing the degenerate base and/or universal base in a predetermined allowable number into the plurality of probing sequences at a position(s) mismatched with each other in the plurality of sequence patterns for each of the at least two candidate probing regions such that the plurality of sequence patterns are maximally matched with each other; and wherein the step (c) is performed by determining as a probing region for detecting all or a part of the plurality of target nucleic acid sequences, among the at least two candidate probing regions, (i) a candidate probing region of a sequence pattern in which the maximum matching is not less than the predetermined coverage and the highest maximum matching is shown, (ii) a candidate probing region of a sequence pattern in which the maximum matching is not less than the predetermined coverage and a minimum number of the degenerate base and/or universal base is introduced for the maximum matching, or (iii) a candidate probing region of a sequence pattern in which the maximum matching is not less than the predetermined coverage, the highest maximum matching is shown and a minimum number of the degenerate base and/or universal base is introduced for the maximum matching.

By grouping the plurality of probing sequences according to sequence identity to obtain a plurality of sequence patterns, it is possible to reduce the number of probing sequences as a comparison subject for whether to be matched or mismatched, thereby reducing a time for determining the probing region.

The above-described steps (b) and (c) are also applied to a plurality of sequence patterns of a plurality of probing sequences.

According to an embodiment of the present invention, the plurality of sequence patterns each has a unique serial number.

According to an embodiment, the reference probing sequence is a probing sequence of a sequence pattern having the largest number of probing sequences among the plurality of sequence patterns.

The other feature of the present invention is to the application of linear programming as optimization logic, in determining as a probing region by optimally introducing a degenerate base and/or universal base in a predetermined allowable number into a plurality of probing sequences in a candidate probing region.

Since the description of a linear programming in the second method of the present invention is the same as that of the first method of the present invention, the common descriptions between them are omitted in order to avoid undue redundancy leading to the complexity of this specification.

According to an embodiment of the present invention, the step (b) is performed to achieve the following objective formula 3 together with satisfying the following constraint formulas 5 and 6:

$$\text{Max:} \sum_{i=1}^{r} x_i \qquad \text{Objective formula 3}$$

wherein Max: represents maximization; $x_i$ is a binary variable consisting of a non-selection value ($x_{non\text{-}sel}$) and a selection value ($x_{sel}$) for whether or not the $i^{th}$ probing sequence of the plurality of probing sequences is selected; and i is a serial number of probing sequences ranging from 1 to r;

$$\sum_{j=1}^{c} d_j \leq D_{Lim} \qquad \text{Constraint formula 5}$$

wherein $d_j$ is a binary variable consisting of a non-introduction value ($d_{non\text{-}int}$) and an introduction value ($d_{int}$) representing whether to introduce the degenerate base and/or universal base at the $j^{th}$ position of the plurality of probing sequences or the reference probing sequence; j is a serial number of positions of the probing sequence or the reference probing sequence ranging from 1 to c; and $D_{Lim}$ is a limited number of the degenerate base and/or universal base introduced into the plurality of probing sequences or the reference probing sequence;

$$x_i \leq \min\{a_{i,j}+d_j\} \text{ for all } i,j \quad \text{Constraint formula 6}$$

wherein $x_i$ is a binary variable consisting of a non-selection value ($x_{non-sel}$) and a selection value ($x_{sel}$) for whether or not the $i^{th}$ probing sequence of the plurality of probing sequences is selected; $a_{i,j}$ is a binary constant representing whether the plurality of probing sequences is matched or mismatched with each other at the $j^{th}$ position or the $i^{th}$ probing sequence is matched or mismatched at the $j^{th}$ position with the reference probing sequence; $d_j$ is a binary variable consisting of a non-introduction value ($d_{non-int}$) and an introduction value ($d_{int}$) representing whether to introduce the degenerate base and/or universal base at the $j^{th}$ position of the plurality of probing sequences or the reference probing sequence; $a_{i,j}+d_j$ is a binary variable representing whether the plurality of probing sequences with or without the introduced degenerate base and/or universal base is matched or mismatched with each other at the $j^{th}$ position or the reference probing sequence with or without the introduced degenerate base and/or universal base is matched or mismatched at the $j^{th}$ position with the $i^{th}$ probing sequence; $\{a_{i,j}+d_j\}$ represents a set including $a_{i,j}+d_j$ as elements; min $\{a_{i,j}+d_j\}$ represents a minimum value among the elements of the set $\{a_{i,j}+d_j\}$; and for all i, j represents application to all positions of all the probing sequences.

In order to apply the objective formula 1, the constraint formulas 1 and 2 to a method for determining a probing region, the objective formula 1, the constraint formulas 1 and 2 are reconstructed into the objective formula 3, the constraint formulas 5 and 6 for a plurality of probing sequences or a reference probing sequence, which is a comparison reference and subject of a mismatch, and an introduction subject of the degenerate base and/or universal base. Therefore, the objective formula 1, the constraint formulas 1 and 2 is modified to apply to a plurality of probing sequences or a reference probing sequence, which is a comparison reference and subject of a mismatch, and an introduction subject of the degenerate base and/or universal base, providing the objective formula 3, the constraint formulas 5 and 6. In addition, the common descriptions between the objective formula 1, the constraint formulas 1 and 2, and the objective formula 3, the constraint formulas 5 and 6 are omitted in order to avoid undue redundancy leading to the complexity of this specification.

When the method further comprises, between the steps (a) and (b), (a-1) grouping the plurality of probing sequences according to sequence identity to obtain a plurality of sequence patterns; or the method further comprises, between the steps (a) and (b), (a-1) grouping the plurality of probing sequences of each of the at least two candidate probing regions according to sequence identity to obtain a plurality of sequence patterns, the step (b) of the present invention may be carried out as follows.

According to an embodiment, the step (b) is performed to achieve the following objective formula 4 together with satisfying the following constraint formulas 7 and 8:

$$\text{Max: } \sum_{i=1}^{r} p_i x_i \quad \text{Objective formula 4}$$

wherein Max: represents maximization; is the number of probing sequences belonging to the $i^{th}$ sequence pattern of probing sequences; $x_i$ is a binary variable consisting of a non-selection value ($x_{non-sel}$) and a selection value ($x_{sel}$) for whether or not the $i^{th}$ sequence pattern of probing sequences is selected; and i is a serial number of sequence patterns of probing sequences ranging from 1 to r;

$$\sum_{j=1}^{c} d_j \leq D_{Lim} \quad \text{Constraint formula 7}$$

wherein $d_j$ is a binary variable consisting of a non-introduction value ($d_{non-int}$) and an introduction value ($d_{int}$) representing whether to introduce the degenerate base and/or universal base at the $j^{th}$ position of the probing sequence of the sequence pattern or the reference probing sequence; j is a serial number of positions of the probing sequence of the sequence pattern or the reference probing sequence ranging from 1 to c; and $D_{Lim}$ is a limited number of the degenerate base and/or universal base introduced into the probing sequence of the sequence pattern or the reference probing sequence;

$$x_i \leq \min\{a_{i,j}+d_j\} \text{ for all } i,j \quad \text{Constraint formula 8}$$

wherein $x_i$ is a binary variable consisting of a non-selection value ($x_{non-sel}$) and a selection value ($x_{sel}$) for whether or not the $i^{th}$ sequence pattern of probing sequences is selected; $a_{i,j}$ is a binary constant representing whether probing sequences of each of the sequence patterns are matched or mismatched with each other at the $j^{th}$ position or a probing sequence of the $i^{th}$ sequence pattern is matched or mismatched at the $j^{th}$ position with the reference probing sequence; $d_j$ is a binary variable consisting of a non-introduction value ($x_{non-int}$) and an introduction value ($d_{int}$) representing whether to introduce the degenerate base and/or universal base at the $j^{th}$ position of the probing sequence of each of the sequence patterns or the reference probing sequence; $a_{i,j}+d_j$ is a binary variable representing whether the probing sequences of each of the sequence patterns with or without the introduced degenerate base and/or universal base are matched or mismatched with each other at the $j^{th}$ position or the reference probing sequence with or without the introduced degenerate base and/or universal base is matched or mismatched at the $j^{th}$ position with the probing sequence of the $i^{th}$ sequence pattern; $\{a_{i,j}+d_j\}$ represents a set including $a_{i,j}+d_j$ as elements; min $\{a_{i,j}+d_j\}$ represents a minimum value among the elements of the set $\{a_{i,j}+d_j\}$; and for all i, j represents application to all positions of all the probing sequences.

In order to apply the objective formula 3, the constraint formulas 5 and 6 to a plurality of sequence patterns of a plurality of probing sequences, the objective formula 3, the constraint formulas 5 and 6 are reconstructed into the objective formula 4, the constraint formulas 7 and 8 for a plurality of sequence patterns. Therefore, the variables and constants for the plurality of probing sequences in the objective formula 3, the constraint formulas 5 and 6 are modified for the plurality of sequence patterns in the objective formula 4, the constraint formulas 7 and 8. In addition, the common descriptions between the objective formula 3, the constraint formulas 5 and 6, and the objective formula 4, the constraint formulas 7 and 8 are omitted in order to avoid undue redundancy leading to the complexity of this specification.

III. Storage Medium, Device and Program

In another aspect of this invention, there is provided a computer readable storage medium containing instructions to configure a processor to perform a method for preparing an oligonucleotide for detecting a plurality of target nucleic acid sequences having sequence similarity with a maximum target coverage, the method comprising: (a) selecting each of sequences with sequence similarity in the same region of a plurality of target nucleic acid sequences as an oligonucleotide to prepare a plurality of oligonucleotides; (b) selecting one of the plurality of oligonucleotides as a reference oligonucleotide; and (c) introducing a degenerate base and/or universal base in a predetermined allowable number into the reference oligonucleotide at a position(s) mismatched between the reference oligonucleotide and the plurality of oligonucleotides to be maximally matched with the plurality of oligonucleotides, and selecting as a sequence of an oligonucleotide a sequence of the reference oligonucleotide into which at least one of the degenerate base and/or the universal bases is introduced, thereby preparing an oligonucleotide with a maximum target coverage.

In still another aspect of this invention, there is provided a computer program to be stored on a computer readable storage medium, to configure a processor to perform a method for preparing an oligonucleotide for detecting a plurality of target nucleic acid sequences having sequence similarity with a maximum target coverage, and the method is the same as the method described in the computer readable storage medium described above.

In another aspect of this invention, there is provided a device for preparing an oligonucleotide for detecting a plurality of target nucleic acid sequences having sequence similarity with a maximum target coverage, comprising (a) a computer processor, and (b) a computer readable storage medium of the present method coupled to the computer processor.

In another aspect of this invention, there is provided a computer readable storage medium containing instructions to configure a processor to perform a method for determining a probing region in a plurality of target nucleic acid sequences having sequence similarity, the method comprising: (a) selecting one candidate probing region in a plurality of target nucleic acid sequences and providing sequences in the candidate probing region as a plurality of probing sequences; (b) introducing a degenerate base and/or universal base in a predetermined allowable number into the plurality of probing sequences at a position(s) mismatched between the plurality of probing sequences such that the plurality of probing sequences are maximally matched with each other; and (c) determining the candidate probing region as a probing region far detecting all or a part of the plurality of target nucleic acid sequences when the maximum matching is not less than a predetermined coverage.

In still another aspect of this invention, there is provided a computer program to be stored on a computer readable storage medium, to configure a processor to perform a method for determining a probing region in a plurality of target nucleic acid sequences having sequence similarity, and the method is the same as the method described in the computer readable storage medium described above.

In still another aspect of this invention, there is provided a device for determining a probing region in a plurality of target nucleic acid sequences having sequence similarity, comprising (a) a computer processor, and (b) a computer readable storage medium of the present method coupled to the computer processor.

Since the storage medium, the device and the computer program of the prevent invention are intended to perform the present methods described hereinabove in a computer, the common descriptions between them are omitted in order to avoid undue redundancy leading to the complexity of this specification.

The program instructions are operative, when performed by the processor, to cause the processor to perform the present method described above. The program instructions for performing the method for preparing an oligonucleotide described above may comprise the following instructions: (i) an instruction to select each of sequences with sequence similarity in the same probing region of a plurality of target nucleic acid sequences as a probing sequence or an oligonucleotide to prepare a plurality of probing sequences or a plurality of oligonucleotides; (ii) an instruction to select one of the plurality of probing sequences as a reference probing sequence or to one of the plurality of oligonucleotides as a reference oligonucleotide; (iii) an instruction to introduce a degenerate base and/or universal base in a predetermined allowable number into the reference probing sequence or the reference oligonucleotide at a position(s) mismatched between the reference probing sequence or the reference oligonucleotide and the plurality of probing sequences or the plurality of oligonucleotides to be maximally matched with the plurality of probing sequences or the plurality of oligonucleotides; (iv) an instruction to select as a sequence of an oligonucleotide the reference probing sequence or a sequence of the reference oligonucleotide into which at least one of the degenerate base and/or the universal base is introduced, thereby preparing an oligonucleotide with a maximum target coverage. In addition, the program instructions may include at least one of the following instructions: (v) an instruction to collect a plurality of target nucleic acid sequences from a database for nucleic acid sequences, and (vi) an instruction to align a plurality of target nucleic acid sequences.

The storage medium and the device of the present invention may include a database of nucleic acid sequences.

The present method is implemented in a processor, such as a processor in a stand-alone computer or a network attached computer.

The types of the computer readable storage medium include various storage medium such as CD-R, CD-ROM, DVD, flash memory, floppy disk, hard drive, portable HDD, USB, magnetic tape, MINIDISC, nonvolatile memory card, EEPROM, optical disk, optical storage medium, RAM, ROM, system memory and web server.

The oligonucleotide, target nucleic acid sequences and/or a probing region prepared by the present invention may be provided in a variety of ways. For example, the prepared oligonucleotide, target nucleic acid sequences and/or a probing region may be provided to a separate system such as a desktop computer system via a network connection (e.g., LAN, VPN, intranet and internet) or direct connection (e.g., USB or other direct wired or wireless connection), or provided on a portable medium such as a CD, DVD, floppy disk and portable HDD. Similarly, the prepared oligonucleotide, target nucleic acid sequences and/or a probing region may be provided to a server system via a network connection (e.g., LAN, VPN, internet, intranet and wireless communication network) to a client such as a notebook or a desktop computer system.

The instructions to configure the processor to perform the present invention may be included in a logic system. The instructions may be downloaded and stored in a memory module (e.g., hard drive or other memory such as a local or attached RAM or ROM), although the instructions can be provided on any software storage medium such as a portable HDD, USB, floppy disk, CD and DVD. A computer code for implementing the present invention may be implemented in a variety of coding languages such as C, C++, Java, Visual Basic, VBScript, JavaScript, Perl and XML. In addition, a variety of languages and protocols may be used in external and internal storage and transmission of data and commands according to the present invention.

The computer processor may be prepared in such a manner that a single processor can do several performances. Alternatively, the processor unit may be prepared in such a manner that several processors do the several performances, respectively.

The features and advantages of this invention are summarized as follows:

(a) In designing an oligonucleotide for detecting a plurality of nucleic acid sequences of a target nucleic acid molecule exhibiting genetic diversity with a maximum target coverage, the present invention provides a more logical and efficient method by adopting a strategy of selecting a reference probing sequence or a reference oligonucleotide to prepare an oligonucleotide into which degenerate bases and/or universal bases are introduced. According to one embodiment of the present invention, the present invention prepares an oligonucleotide having a maximum target coverage into which an appropriate number of degenerate bases are introduced in sllico manner, by converting a logic adopted in the present invention into a mathematical logic and being computer programmed.

(b) The present invention takes into account both a target coverage and an efficiency of oligonucleotides in preparing oligonucleotide into which the degenerate bases and/or the universal bases are introduced. Degenerate base-introduced oligonucleotides increase a target coverage but they have the problem of reducing the efficiency of oligonucleotides, particularly greatly causing interference between oligonucleotides in multiplex detection. Therefore, the oligonucleotide should be prepared considering both the target coverage and the number of degenerate bases to be introduced, and this technical purpose is achieved by the present invention. According to the present invention, an optimal oligonucleotide can be presented in a more logical and efficient manner in terms of the target coverage and the efficiency of the oligonucleotide.

(c) When degenerate bases and/or universal bases are introduced into an oligonucleotide in order to detect a plurality of nucleic acid sequences of a target nucleic acid molecule exhibiting genetic diversity with a maximum target coverage, empirical and manual methods have been conventionally utilized, which are a time-consuming and labor-consuming process with poor speed and accuracy.

According to an embodiment, unlike the conventional methods described above, the present invention may present an optimal introduction of degenerate bases and/or universal bases into an oligonucleotide in a logical and automatic manner. In presenting an optimal introduction of degenerate bases and/or universal bases into an oligonucleotide, the method of the present invention is much more rapid and accurate than any conventional method.

(d) According to an embodiment of the present invention, the optimization logic of the present invention may be used in (i) the preparation of an oligonucleotide into which a limited number of degenerate bases and/or universal bases are introduced for detecting a plurality of target nucleic acid sequences with a maximum target coverage, and (ii) the determination of a probing region in a plurality of target nucleic acid sequences.

The present invention will now be described in further detail by examples. It would be obvious to those skilled in the art that these examples are intended to be more concretely illustrative and the scope of the present invention as set forth in the appended claims is not limited to or by the examples.

EXAMPLES

Example 1: Alignment of Target Nucleic Acid Sequences and Classification (Grouping) of Sequence Patterns 5' UTR sequences of Enterovirus as a plurality of target nucleic acid sequences collected from National Center for Biotechnology Information (NCBI) were aligned and the collected sequences were classified into sequence patterns according to sequence identity. As a result, in a total of 531 target nucleic acid sequences, a total of 20 sequence patterns were classified for one region showing sequence similarity, and among these, the sequence of the $20^{th}$ sequence pattern containing the largest number of identical sequences was selected as a reference nucleic acid sequence (i.e., a reference oligonucleotide). Sequence patterns containing sequences having three or less variations compared to the reference nucleic acid sequence were summarized in Table 1 below.

TABLE 1

| i | Oligonucleotide sequence | $p_i$ |
|---|---|---|
| 1 | C A  T C  A G  G C  C C  C T  G A A T G C G G | 1 |
| 2 | C T  T C  C G  T C  C C  C T  G A A T G C G T | 1 |
| 3 | C G  T C  C G  G C  C C  C T  G A A T G C G G | 3 |
| 4 | C C  A C  C G  G C  C C  C T  G C A T G C G G | 1 |
| 5 | C C  A C  C G  G C  C C  C T  G A A T G C G G | 1 |
| 6 | C C  T G  C G  G C  C C  C T  G C T T G C G G | 1 |
| 7 | C C  T C  G G  G C  A C  C T  G A A T G C G G | 2 |
| 8 | C C  T C  C A  G C  C C  C T  G A A T G C G T | 1 |
| 9 | C C  T C  C G  T G  C T  C T  G A A T G C G G | 5 |
| 10 | C C  T C  C G  G G  C C  C T  G A T T G C T G | 1 |
| 11 | C C  T C  C G  G A  C C  C T  G A A T A C G T | 3 |
| 12 | C C  T C  C G  G C  A C  C T  G A A T G G G G | 2 |
| 13 | C C  T C  C G  G C  C C  C A  G A A T G A G G | 2 |
| 14 | C C  T C  C G  G C  C C  C C  G A A T G C G G | 1 |
| 15 | C C  T C  C G  G C  C C  C T  G A A A G C G G | 1 |
| 16 | C C  T C  C G  G C  C C  C T  G A A T G G A C | 1 |
| 17 | C C  T C  C G  G C  C C  C T  G A A T G G G C | 1 |
| 18 | C C  T C  C G  G C  C C  C T  G A A T G A G G | 86 |
| 19 | C C  T C  C G  G C  C C  C T  G A A T G C T G | 4 |
| 20 | C C  T C  C G  G C  C C  C T  G A A T G C G G | 413 | i in Table 1 is a serial number of sequence patterns and sequences of sequence patterns are SEQ ID Nos:1 to 20, respectively. The numbers ($p_i$) in Table 1 represent the number of target nucleic acid sequences belonging to each sequence pattern. The sequence patterns in Table 1 serve as both target nucleic acid sequences to be detected and oligonucleotide sequences (primers and/or probes). For example, when a probe is designed by using a nucleic acid sequence of the $20^{th}$ sequence pattern of Table 1, it may be used to detect a nucleic acid sequence containing a sequence complementary to the nucleic acid sequence of the $20^{th}$ sequence pattern. When a probe is designed by using a sequence complementary to the nucleic acid sequence of the $20^{th}$ sequence pattern, it may be used to detect a nucleic acid sequence containing the nucleic acid sequence of the $20^{th}$ sequence pattern. In the following Examples, probes are represented by the sequences in Table 1, particularly for introducing degenerate bases (a reference probe: a probe of $20^{th}$ sequence pattern, a total number of probes of 20 sequence patterns: 531).

Example 2: Introduction of a Limited Number (Three) of Degenerate Bases into a Probe to be Maximally Matched Between Probes Using Linear Programming Algorithm When one probe is used to detect the plurality of target nucleic acid sequences with a maximum target coverage, a linear programming algorithm was applied to provide an optimization logic suitable for optimal application of degenerate bases to the probe.

Twenty (20) sequence patterns shown in Table 1 were used. Since a probe to be provided should detect target nucleic acid sequences with a maximum target coverage and introduce degenerate bases at mismatch positions of the probe, $x_i$ and $d_j$ were set as a decision variable. Here, $x_i$ is a binary variable consisting of a non-selection value ($x_{non-sel}=0$) and a selection value ($x_{Sel}=1$) for whether or not the $i^{th}$ sequence pattern of probes is selected, $d_j$ is a binary variable consisting of a non-introduction value ($d_{non-int}=0$) and an introduction value ($d_{int}=1$) representing whether to introduce a degenerate base at the $j^{th}$ position of the reference probe (the reference nucleic acid sequence of Example 1 is provided as the reference probe). i is a serial number of sequence patterns of probes ranging from 1 to 20, j is a serial number of the position of the reference probe ranging from 1 to 20.

An objective function is maximization of the number of probes belonging to the selected probe sequence patterns (i.e., $Z=1x_1+1x_2+3x_3+1x_4+1x_5+1x_6+2x_7+1x_8+5x_9+1x_{10}+3x_{11}+2x_{12}+2x_{13}+1x_{14}+1x_{15}+1x_{16}+1x_{17}+86x_{18}+4x_{19}+413x_{20}$).

Since the introduction of a limited number (three) of degenerate bases into the probe is intended, a constraint formula can be expressed as $d_1+d_2+d_3+d_4+d_5+d_6+d_7+d_8+d_9+d_{10}+d_{11}+d_{12}+d_{13}+d_{14}+d_{15}+d_{16}+d_{17}+d_{18}+d_{19}+d_{20} \leq 3$.

In order to use the linear programming algorithm in consideration of the probe sequence match pattern of Example 1, the probe of the $20^{th}$ sequence pattern in the probe sequences of Table 1 was adopted as the reference probe. $a_{i,j}$ is 1 when each of probe sequences is matched with the reference probe and $a_{i,j}$ is 0 when it is not matched. The results were shown in FIG. 1 as a matrix $A=\{a_{i,j}\}$.

As shown in FIG. 1, when the sequence pattern of the probe is perfectly matched with the reference probe such as the element of the $20^{th}$ line (i=20), $a_{i,j}$ is 1 for all j, it was found that a minimum value of $a_{i,j}$ is 1.

In addition, for maximally matching between the reference probe and the probe sequence patterns, required is a constraint formula related to whether or not the reference probe is matched with the probe sequence patterns before and after introducing degenerate bases into the reference probe. The 17, 18, 19 and $20^{th}$ patterns (i=17, 18, 19, 20) in FIG. 1 were summarized in Table 2 for description of the constraint formula.

TABLE 2

| j | 1 | 2 | 3 | 4 | 5 | 6 | 7 | 8 | 9 | 10 | 11 | 12 | 13 | 14 | 15 | 16 | 17 | 18 | 19 | 20 | |
|---|---|---|---|---|---|---|---|---|---|---|---|---|---|---|---|---|---|---|---|---|---|
| $a_{17,j}$ | 1 | 1 | 1 | 1 | 1 | 1 | 1 | 1 | 1 | 1 | 1 | 1 | 1 | 1 | 1 | 1 | 1 | 0 | 1 | 0 | Not selectable |
| $a_{18,j}$ | 1 | 1 | 1 | 1 | 1 | 1 | 1 | 1 | 1 | 1 | 1 | 1 | 1 | 1 | 1 | 1 | 1 | 0 | 1 | 1 | Not selectable |
| $a_{19,j}$ | 1 | 1 | 1 | 1 | 1 | 1 | 1 | 1 | 1 | 1 | 1 | 1 | 1 | 1 | 1 | 1 | 1 | 1 | 0 | 1 | Not selectable |
| $a_{20,j}$ | 1 | 1 | 1 | 1 | 1 | 1 | 1 | 1 | 1 | 1 | 1 | 1 | 1 | 1 | 1 | 1 | 1 | 1 | 1 | 1 | Selectable |
| $d_j$ | 0 | 0 | 0 | 0 | 0 | 0 | 0 | 0 | 0 | 0 | 0 | 0 | 0 | 0 | 0 | 0 | 0 | 1 | 0 | 1 | |
| $a_{17,j} + d_j$ | 1 | 1 | 1 | 1 | 1 | 1 | 1 | 1 | 1 | 1 | 1 | 1 | 1 | 1 | 1 | 1 | 1 | 1 | 1 | 1 | Selectable |
| $a_{18,j} + d_j$ | 1 | 1 | 1 | 1 | 1 | 1 | 1 | 1 | 1 | 1 | 1 | 1 | 1 | 1 | 1 | 1 | 1 | 1 | 1 | 2 | Selectable |
| $a_{19,j} + d_j$ | 1 | 1 | 1 | 1 | 1 | 1 | 1 | 1 | 1 | 1 | 1 | 1 | 1 | 1 | 1 | 1 | 1 | 2 | 0 | 2 | Not selectable |
| $a_{20,j} + d_j$ | 1 | 1 | 1 | 1 | 1 | 1 | 1 | 1 | 1 | 1 | 1 | 1 | 1 | 1 | 1 | 1 | 1 | 2 | 1 | 2 | Selectable |

In expression of whether or not the reference probe is matched with a probe prior to the introduction of degenerate bases, $a_{i,j}$ is a binary constant representing whether a probe belonging to the $i^{th}$ sequence pattern of probes is matched or mismatched at the $j^{th}$ position with the reference probe, and a non-matching value and a matching value of $a_{i,j}$ are 0 and 1, respectively. Particularly, when the probe of the $20^{th}$ pattern in Table 2 is selected as the reference probe, it has the matching value of 1 (i.e., $a_{20,j}=1$) at all positions of the probe. However, since the probe of the $17^{th}$ pattern is mismatched at positions 18 and 20, $a_{17,18}$ and $d_{17,20}$ were represented by 0, and the other positions were represented by 1 ($a_{17,j}=1$) because they are matched. The probe of the $18^{th}$ pattern with a mismatch at the $18^{th}$ position ($a_{18,18}=0$) was described by using a binary constant for whether it is matched or mismatched with the probe of the $20^{th}$ pattern (the reference probe). The probe of the $19^{th}$ pattern was found to be matched or mismatched with the probe of the $20^{th}$ pattern (the reference probe), describing as 0 only at the $19^{th}$ position ($a_{19,19}=0$) and 1 at the other positions. In short, $a_{i,j}$ of the probe of the $20^{th}$ pattern is expressed as 1 because it is perfectly matched with the reference probe, but $a_{i,j}$ of the probes of the 17-$19^{th}$ patterns as 1 and 0 because they include positions matched or mismatched with the reference probe.

In Table 2, when a limited number (e.g., two) of degenerate bases are introduced into the reference probe to become perfectly matched with the probes of the 17 and $18^{th}$ patterns, degenerate bases were introduced at positions 18 and 20 of the reference probe to be matched with the probes of the 17 and 18$^{th}$ patterns. Whether the reference probe with or without the introduced degenerate base is matched or mismatched at the j$^{th}$ position with a probe belonging to the i$^{th}$ sequence pattern of probes was represented as a binary variable, $a_{i,j}+d_j$.

Because the probes of the 17$^{th}$ and 18$^{th}$ patterns were all matched with the reference probes by introducing the degenerate bases at positions 18 and 20 of the reference probe, $a_{i,j}+d_j$ of probes of the 17$^{th}$ and 18$^{th}$ patterns were all 1 or more. On the other hand, since the probe of the 19$^{th}$ pattern was still not matched at the position 19, it was found that $a_{19,19}+d_{19}$ has a value of zero.

Therefore, in order to select probe patterns matched with a reference probe by introducing degenerate bases into the reference probe, it has to have a minimum value of 1 for $a_{i,j}+d_j$ at all positions. When the minimum value is 0, this means that the probe patterns are mismatched with the reference probe at at least one position of the probe patterns. Such probe patterns cannot be selected.

In other words, a constraint formula for selection of the i$^{th}$ probe pattern in terms of match/mismatch and introduction of degenerate bases is $x_i \leq \min \{a_{i,j}+d_j,$ for all j$\}$, which means that $x_i \leq a_{i,j}+d_j$ needs to be satisfied for all j in obtaining solutions by using the linear programming algorithm.

Where the constraint formula is applied to all the sequence patterns in Table 1, each sequence pattern has to satisfy the following: $x_i \leq a_{i,1}+d_1$, $x_i \leq a_{i,2}+d_2$, $x_i \leq a_{i,3}+d_3$, $x_i \leq a_{i,4}+d_4$, $x_i \leq a_{i,5}+d_5$, $x_i \leq a_{i,6}+d_6$, $x_i \leq a_{i,7}+d_7$, $x_i \leq a_{i,8}+d_8$, $x_i \leq a_{i,9}+d_9$, $x_i \leq a_{i,10}+d_{10}$, $x_i \leq a_{i,11}+d_{11}$, $x_i \leq a_{i,12}+d_{12}$, $x_i \leq a_{i,13}+d_{13}$, $x_i \leq a_{i,14}+d_{14}$, $x_i \leq a_{i,15}+d_{15}$, $x_i \leq a_{i,16}+d_{16}$, $x_i \leq a_{i,17}+d_{17}$, $x_i \leq a_{i,18}+d_{18}$, $x_i \leq a_{i,19}+d_{19}$, and $x_i \leq a_{i,20}+d_{20}$.

An optimal solution of the linear programming problem was obtained using program MATLAB R2015b (MathWorks) to achieve the objective formula together with satisfying the constraint formulas. The result was calculated as $d_2=1$, $d_{18}=1$ and $d_{19}=1$ at positions j=2, 18 and 19 and $d_j=0$ at the other positions, and calculated as $x_3=1$, $x_{18}=1$, $x_{19}=1$, and $x_{20}=1$ for sequence patterns i=3, 18, 19 and 20 and $x_i=0$ for the other sequence patterns.

It was found that when the degenerate bases were introduced at positions j=2, 18 and 19 of the reference probe, the introduced reference probe was matched with the sequence patterns of i=3, 18, 19 and 20, the number of probes included in the sequence patterns of i=3, 18, 19 and 20 is $p_3=3$, $p_{18}=86$, $p_{19}=4$ and $p_{20}=413$, respectively and 506 probes out of a total of 531 probes were matched with the reference probe (matching rate 95.3%).

After determining that the degenerate bases have to be introduced at positions 2, 18 and 19 of the reference probe, the degenerate base S (G or C) was introduced at j=2, the degenerate base M (A or C) at j=18, and the degenerate base K (G or T) at j=19. Using the probes into which the degenerate bases were introduced, it was verified that the maximum target coverage for the plurality of target nucleic acid sequences in Table 1 is 95.3%.

Example 3: Verification of the Optimal Solution of the Linear Programming Problem The optimal solution of the linear programming problem obtained in Example 2 was verified. First, in the probe sequences of Table 1, the probe of the 20th sequence pattern was used as the reference probe. $a_{i,j}$ was represented by 1 when a sequence pattern is matched with the reference probe and represented by 0 when a sequence pattern is not matched. The minimum values of $a_{i,j}$ in each sequence pattern were shown in Table 3 and the results were summarized.

TABLE 3

| i | Oligonucleotide sequence | $p_i$ | min ($a_{i,j}$) |
|---|---|---|---|
| 1  | 1 0 1 1 0 1 1 1 1 1 1 1 1 1 1 1 1 1 1 1 | 1   | 0 |
| 2  | 1 0 1 1 1 1 0 1 1 1 1 1 1 1 1 1 1 1 1 0 | 1   | 0 |
| 3  | 1 0 1 1 1 1 1 1 1 1 1 1 1 1 1 1 1 1 1 1 | 3   | 0 |
| 4  | 1 1 0 1 1 1 1 1 1 1 1 1 0 1 1 1 1 1 1 1 | 1   | 0 |
| 5  | 1 1 0 1 1 1 1 1 1 1 1 1 1 1 1 1 1 1 1 1 | 1   | 0 |
| 6  | 1 1 1 0 1 1 1 1 1 1 1 1 0 0 1 1 1 1 1 1 | 1   | 0 |
| 7  | 1 1 1 1 1 0 1 1 0 1 1 1 1 1 1 1 1 1 1 1 | 2   | 0 |
| 8  | 1 1 1 1 1 0 1 1 1 1 1 1 1 1 1 1 1 1 1 0 | 1   | 0 |
| 9  | 1 1 1 1 1 1 0 0 1 0 1 1 1 1 1 1 1 1 1 1 | 5   | 0 |
| 10 | 1 1 1 1 1 1 1 0 1 1 1 1 1 0 1 1 1 0 1 1 | 1   | 0 |
| 11 | 1 1 1 1 1 1 1 1 0 1 1 1 1 1 1 1 0 1 1 0 | 3   | 0 |
| 12 | 1 1 1 1 1 1 1 1 0 1 1 1 1 1 1 1 0 1 1 1 | 2   | 0 |
| 13 | 1 1 1 1 1 1 1 1 1 1 0 1 1 1 1 1 0 1 1 1 | 2   | 0 |
| 14 | 1 1 1 1 1 1 1 1 1 1 0 1 1 1 1 1 1 1 1 1 | 1   | 0 |
| 15 | 1 1 1 1 1 1 1 1 1 1 1 1 1 1 1 0 1 1 1 1 | 1   | 0 |
| 16 | 1 1 1 1 1 1 1 1 1 1 1 1 1 1 1 1 0 0 0 0 | 1   | 0 |
| 17 | 1 1 1 1 1 1 1 1 1 1 1 1 1 1 1 1 1 0 1 0 | 1   | 0 |
| 18 | 1 1 1 1 1 1 1 1 1 1 1 1 1 1 1 1 1 0 1 1 | 86  | 0 |
| 19 | 1 1 1 1 1 1 1 1 1 1 1 1 1 1 1 1 1 1 0 1 | 4   | 0 |
| 20 | 1 1 1 1 1 1 1 1 1 1 1 1 1 1 1 1 1 1 1 1 | 413 | 1 |

In addition, the solution of Example 2, "$d_2=1$, $d_{18}=1$ and $d_{19}=1$ at positions j=2, 18 and 19, and $d_j=0$ at the other positions" for introducing three or less degenerate bases was input to Table 3 to obtain the minimum value of $a_{i,j}+d_j$ in each sequence pattern. The results are summarized in Table 4.

TABLE 4

| $d_j$ | 0 | 1 | 0 0 0 0 0 0 0 0 0 0 0 0 0 0 0 0 | 1 | 1 | 0 | | |
|---|---|---|---|---|---|---|---|---|

| | | | Oligonucleotide sequence | | | | | |
|---|---|---|---|---|---|---|---|---|
| i | +1 | | | +1 | +1 | $p_i$ | min($a_{i,j}$) | min($a_{i,j}+d_j$) |
| 1  | 1 | 1 | 1 0 1 1 1 1 1 1 1 1 1 1 1 1 1 1 | 2 | 1 | 1 | 1 | 0 | 0 |
| 2  | 1 | 1 | 1 1 1 0 1 1 1 1 1 1 1 1 1 1 1 1 | 2 | 1 | 0 | 1 | 0 | 0 |
| 3  | 1 | 1 | 1 1 1 1 1 1 1 1 1 1 1 1 1 1 1 1 | 2 | 1 | 1 | 3 | 0 | 1 |
| 4  | 1 | 2 | 0 1 1 1 1 1 1 1 1 1 1 1 0 1 1 1 | 2 | 1 | 1 | 1 | 0 | 0 |
| 5  | 1 | 2 | 0 1 1 1 1 1 1 1 1 1 1 1 1 1 1 1 | 2 | 1 | 1 | 1 | 0 | 0 |
| 6  | 1 | 2 | 1 0 1 1 1 1 1 1 1 1 1 1 0 0 1 1 | 2 | 1 | 1 | 1 | 0 | 0 |
| 7  | 1 | 2 | 1 1 0 1 1 0 1 1 1 1 0 1 1 1 1 1 | 2 | 1 | 1 | 2 | 0 | 0 |
| 8  | 1 | 2 | 1 1 1 0 1 1 1 1 1 1 1 0 1 1 1 1 | 2 | 1 | 0 | 1 | 0 | 0 |
| 9  | 1 | 2 | 1 1 1 1 0 0 1 0 1 1 1 0 1 1 1 1 | 2 | 1 | 1 | 5 | 0 | 0 |
| 10 | 1 | 2 | 1 1 1 1 1 0 1 1 1 1 1 1 1 0 1 1 | 2 | 1 | 1 | 1 | 0 | 0 |

TABLE 4-continued

| | | | | | | | | | | | | | | | | | | | | | | | | | | | |
|---|---|---|---|---|---|---|---|---|---|---|---|---|---|---|---|---|---|---|---|---|---|---|---|---|---|---|---|
| 11 | 1 | 2 | 1 | 1 | 1 | 1 | 1 | 0 | 1 | 1 | 1 | 1 | 1 | 1 | 1 | 1 | 1 | 1 | 0 | 2 | 1 | 0 | 3 | 0 | 0 | | |
| 12 | 1 | 2 | 1 | 1 | 1 | 1 | 1 | 0 | 1 | 1 | 1 | 1 | 1 | 1 | 1 | 1 | 1 | 1 | 1 | 1 | 1 | 1 | 2 | 0 | 0 | | |
| 13 | 1 | 2 | 1 | 1 | 1 | 1 | 1 | 1 | 1 | 1 | 1 | 1 | 0 | 1 | 1 | 1 | 1 | 1 | 1 | 1 | 1 | 1 | 2 | 0 | 0 | | |
| 14 | 1 | 2 | 1 | 1 | 1 | 1 | 1 | 1 | 1 | 1 | 1 | 1 | 1 | 0 | 1 | 1 | 1 | 1 | 1 | 2 | 1 | 1 | 1 | 0 | 0 | | |
| 15 | 1 | 2 | 1 | 1 | 1 | 1 | 1 | 1 | 1 | 1 | 1 | 1 | 1 | 1 | 1 | 1 | 1 | 0 | 1 | 2 | 1 | 1 | 1 | 0 | 0 | | |
| 16 | 1 | 2 | 1 | 1 | 1 | 1 | 1 | 1 | 1 | 1 | 1 | 1 | 1 | 1 | 1 | 1 | 1 | 1 | 1 | 1 | 1 | 0 | 1 | 0 | 0 | | |
| 17 | 1 | 2 | 1 | 1 | 1 | 1 | 1 | 1 | 1 | 1 | 1 | 1 | 1 | 1 | 1 | 1 | 1 | 1 | 1 | 1 | 1 | 0 | 1 | 0 | 0 | | |
| 18 | 1 | 2 | 1 | 1 | 1 | 1 | 1 | 1 | 1 | 1 | 1 | 1 | 1 | 1 | 1 | 1 | 1 | 1 | 1 | 1 | 1 | 1 | 86 | 0 | 1 | | |
| 19 | 1 | 2 | 1 | 1 | 1 | 1 | 1 | 1 | 1 | 1 | 1 | 1 | 1 | 1 | 1 | 1 | 1 | 1 | 1 | 2 | 1 | 1 | 4 | 0 | 1 | | |
| 20 | 1 | 2 | 1 | 1 | 1 | 1 | 1 | 1 | 1 | 1 | 1 | 1 | 1 | 1 | 1 | 1 | 1 | 1 | 1 | 2 | 1 | 1 | 413 | 1 | 1 | | |

Then, sequence patterns satisfying $x_i \leq \min\{a_{i,j}+d_j\}$ were selected. The results are shown in Table 5 below.

TABLE 5

| $d_j$ | 0 | 1 | 0 | 0 | 0 | 0 | 0 | 0 | 0 | 0 | 0 | 0 | 0 | 0 | 0 | 0 | 0 | 0 | 0 | 1 | 1 | 0 | | | |
|---|---|---|---|---|---|---|---|---|---|---|---|---|---|---|---|---|---|---|---|---|---|---|---|---|---|

Oligonucleotide sequence

| i | | +1 | | | | | | | | | | | | | | | | | | | +1 | +1 | $p_i$ | $\min(a_{i,j})$ | $\min(a_{i,j}+d_j)$ | |
|---|---|---|---|---|---|---|---|---|---|---|---|---|---|---|---|---|---|---|---|---|---|---|---|---|---|---|
| 1 | 1 | 1 | 1 | 1 | 0 | 1 | 1 | 1 | 1 | 1 | 1 | 1 | 1 | 1 | 1 | 1 | 1 | 1 | 1 | 1 | 2 | 1 | 1 | 1 | 0 | 0 |
| 2 | 1 | 1 | 1 | 1 | 1 | 1 | 0 | 1 | 1 | 1 | 1 | 1 | 1 | 1 | 1 | 1 | 1 | 1 | 1 | 1 | 2 | 1 | 0 | 1 | 0 | 0 |
| 3 | 1 | 1 | 1 | 1 | 1 | 1 | 1 | 1 | 1 | 1 | 1 | 1 | 1 | 1 | 1 | 1 | 1 | 1 | 1 | 1 | 2 | 1 | 1 | 3 | 0 | 1 v |
| 4 | 1 | 2 | 0 | 1 | 1 | 1 | 1 | 1 | 1 | 1 | 1 | 1 | 1 | 1 | 1 | 1 | 0 | 1 | 1 | 1 | 2 | 1 | 1 | 1 | 0 | 0 |
| 5 | 1 | 2 | 0 | 1 | 1 | 1 | 1 | 1 | 1 | 1 | 1 | 1 | 1 | 1 | 1 | 1 | 1 | 1 | 1 | 1 | 2 | 1 | 1 | 1 | 0 | 0 |
| 6 | 1 | 2 | 1 | 0 | 1 | 1 | 1 | 0 | 1 | 1 | 1 | 1 | 1 | 1 | 1 | 1 | 0 | 0 | 1 | 1 | 2 | 1 | 1 | 1 | 0 | 0 |
| 7 | 1 | 2 | 1 | 1 | 0 | 1 | 1 | 1 | 0 | 1 | 1 | 1 | 1 | 1 | 1 | 1 | 1 | 1 | 1 | 1 | 2 | 1 | 1 | 2 | 0 | 0 |
| 8 | 1 | 2 | 1 | 1 | 1 | 0 | 1 | 1 | 1 | 1 | 1 | 1 | 1 | 1 | 1 | 1 | 1 | 1 | 1 | 1 | 2 | 1 | 0 | 1 | 0 | 0 |
| 9 | 1 | 2 | 1 | 1 | 1 | 1 | 0 | 0 | 1 | 0 | 1 | 1 | 1 | 1 | 1 | 1 | 1 | 1 | 1 | 1 | 2 | 1 | 1 | 5 | 0 | 0 |
| 10 | 1 | 2 | 1 | 1 | 1 | 1 | 1 | 0 | 1 | 1 | 1 | 1 | 1 | 1 | 1 | 1 | 0 | 1 | 1 | 1 | 2 | 1 | 1 | 1 | 0 | 0 |
| 11 | 1 | 2 | 1 | 1 | 1 | 1 | 1 | 0 | 1 | 1 | 1 | 1 | 1 | 1 | 1 | 1 | 1 | 1 | 1 | 0 | 2 | 1 | 0 | 3 | 0 | 0 |
| 12 | 1 | 2 | 1 | 1 | 1 | 1 | 1 | 0 | 1 | 1 | 1 | 1 | 1 | 1 | 1 | 1 | 1 | 1 | 1 | 1 | 1 | 1 | 1 | 2 | 0 | 0 |
| 13 | 1 | 2 | 1 | 1 | 1 | 1 | 1 | 1 | 1 | 1 | 1 | 1 | 0 | 1 | 1 | 1 | 1 | 1 | 1 | 1 | 1 | 1 | 1 | 2 | 0 | 0 |
| 14 | 1 | 2 | 1 | 1 | 1 | 1 | 1 | 1 | 1 | 1 | 1 | 1 | 1 | 0 | 1 | 1 | 1 | 1 | 1 | 1 | 2 | 1 | 1 | 1 | 0 | 0 |
| 15 | 1 | 2 | 1 | 1 | 1 | 1 | 1 | 1 | 1 | 1 | 1 | 1 | 1 | 1 | 1 | 1 | 1 | 0 | 1 | 1 | 2 | 1 | 1 | 1 | 0 | 0 |
| 16 | 1 | 2 | 1 | 1 | 1 | 1 | 1 | 1 | 1 | 1 | 1 | 1 | 1 | 1 | 1 | 1 | 1 | 1 | 1 | 1 | 1 | 1 | 0 | 1 | 0 | 0 |
| 17 | 1 | 2 | 1 | 1 | 1 | 1 | 1 | 1 | 1 | 1 | 1 | 1 | 1 | 1 | 1 | 1 | 1 | 1 | 1 | 1 | 1 | 1 | 0 | 1 | 0 | 0 |
| 18 | 1 | 2 | 1 | 1 | 1 | 1 | 1 | 1 | 1 | 1 | 1 | 1 | 1 | 1 | 1 | 1 | 1 | 1 | 1 | 1 | 1 | 1 | 1 | 86 | 0 | 1 v |
| 19 | 1 | 2 | 1 | 1 | 1 | 1 | 1 | 1 | 1 | 1 | 1 | 1 | 1 | 1 | 1 | 1 | 1 | 1 | 1 | 1 | 2 | 1 | 1 | 4 | 0 | 1 v |
| 20 | 1 | 2 | 1 | 1 | 1 | 1 | 1 | 1 | 1 | 1 | 1 | 1 | 1 | 1 | 1 | 1 | 1 | 1 | 1 | 1 | 2 | 1 | 1 | 413 | 1 | 1 |

As shown in Table 5, it was verified that by introducing the degenerate bases into the reference probe, the sequence patterns satisfying $x_i \leq \min\{a_{i,j}+d_j\}$ are i=3, 18 and 19 in addition to the $20^{th}$ sequence pattern, which is consistent with the results obtained in Example 2.

Comparative Example 1: Introduction of a Limited Number (Three) of Degenerate Bases into a Probe to be Maximally Matched Between Probes in Empirical and Manual Manner In order to detect the plurality of target nucleic acid sequences with a maximum target coverage in an empirical and manual manner, three or less degenerate bases were introduced into probes.

Particularly, in 20 sequence patterns shown in Table 1, because the $20^{th}$ sequence pattern include 413 probe sequences having the largest number of identical sequences, and then the $18^{th}$ sequence pattern includes 86 identical sequences, the $20^{th}$ and $18^{th}$ sequence patterns were selected. When the degenerate base was introduced at position 18 (j=18), 499 probe sequences became to be matched with the reference probe. Additionally, when the degenerate base is introduced into the $9^{th}$ sequence pattern having a third largest number of sequences in Table 1, 504 probe sequences became to be matched with the reference probe. In this case, degenerate bases have to be introduced at positions 7, 8, 10 and 18 (j=7, 8, 10 and 18). However, the $20^{th}$, $18^{th}$, and $9^{th}$ sequence patterns cannot be selected because the constraint condition for introducing not more than 3 degenerate bases is not satisfied.

Then, $20^{th}$, $18^{th}$, and $15^{th}$ sequence patterns were selected. Degenerate bases were introduced at positions 16 and 18 (j=16 and 18) such that 413 sequences included in the $20^{th}$ sequence pattern, 86 sequences included in the $18^{th}$ sequence pattern and 1 sequence included in the $15^{th}$ sequence pattern (a total of 500 probe sequences) were matched with the reference probe.

By repeating the manual procedure, it could be determined that when degenerate bases were introduced at positions j=2, 18 and 19 of the reference probe, the reference probe was matched with sequence patterns i=3, 18, 19 and 20 (506 probes among 531 probes). The manual method took about 56 times longer time than the method using the linear programming algorithm (Example 2) for determining the introduction positions of degenerate bases and the selection of the sequence patterns.

Having described a preferred embodiment of the present invention, it is to be understood that variants and modifications thereof falling within the spirit of the invention may become apparent to those skilled in this art, and the scope of this invention is to be determined by appended claims and their equivalents.

This application contains references to amino acid sequences and/or nucleic acid sequences which have been submitted herewith as the sequence listing text file. The aforementioned sequence listing is hereby incorporated by reference in its entirety pursuant to 37 C.F.R. § 1.52(e).

What is claimed is:

1. A computer-implemented method for preparing an oligonucleotide for detecting a plurality of target nucleic acid sequences having sequence similarity with a maximum target coverage, comprising:
   (a) selecting each of sequences with sequence similarity in the same probing region of a plurality of target nucleic acid sequences as a probing sequence or an oligonucleotide sequence to prepare a plurality of probing sequences or a plurality of oligonucleotides;
   (b) selecting one of the plurality of probing sequences as a reference probing sequence or one of the plurality of oligonucleotides as a reference oligonucleotide; and
   (c) introducing a degenerate base and/or universal base in a predetermined allowable number into the reference probing sequence or the reference oligonucleotide at a position(s) mismatched between (i) the reference probing sequence or the reference oligonucleotide and (ii) the plurality of probing sequences or the plurality of oligonucleotides to be maximally matched with the plurality of probing sequences or the plurality of oligonucleotides;
   (d) selecting as a sequence of an oligonucleotide the reference probing sequence or a sequence of the reference oligonucleotide into which at least one of the degenerate base and/or the universal base is introduced; and
   (e) preparing an oligonucleotide with a maximum target coverage with the sequence selected in step (d);
   wherein the step (c) is performed to achieve the following objective formula 1 together with satisfying the following constraint formulas 1 and 2:

$$\text{Max:} \sum_{i=1}^{r} x_i \qquad \text{Objective formula 1}$$

wherein Max: represents maximization; xi is a binary variable consisting of a non-selection value ($x_{non-sel}$) and a selection value ($x_{sel}$) for whether or not the $i^{th}$ probing sequence of the plurality of probing sequences or $i^{th}$ oligonucleotide of the plurality of oligonucleotides is selected; and i is a serial number of probing sequences or oligonucleotides ranging from 1 to r;

$$\sum_{j=1}^{c} d_j \leq D_{Lim} \qquad \text{Constraint formula 1}$$

wherein $d_j$ is a binary variable consisting of a non-introduction value ($d_{non-int}$) and an introduction value ($d_{int}$) representing whether to introduce the degenerate base and/or universal base at the $j^{th}$ position of the reference probing sequence or the reference oligonucleotide; j is a serial number of positions of a reference probing sequence or a reference oligonucleotide ranging from 1 to c ; and $D_{Lim}$ is a limited number of the degenerate base and/or universal base introduced into the reference probing sequence or the reference oligonucleotide;

$$x_i \leq \min\{a_{i,j} + d_j\} \text{ for all } i,j \qquad \text{Constraint formula 2}$$

wherein $x_i$ is a binary variable consisting of a non-selection value ($x_{non-sel}$) and a selection value ($x_{sel}$) for whether or not the $i^{th}$ probing sequence of the plurality of probing sequences or $i^{th}$ oligonucleotide of the plurality of oligonucleotides is selected; $a_{i,j}$ is a binary constant representing whether the $i^{th}$ probing sequence is matched or mismatched at the $j^{th}$ position with the reference probing sequence or the $i^{th}$ oligonucleotide is matched or mismatched at the $j^{th}$ position with the reference oligonucleotide; $d_j$ is a binary variable consisting of a non-introduction value ($d_{non-int}$) and an introduction value ($d_{int}$) representing whether to introduce the degenerate base and/or universal base at the $j^{th}$ position of the reference probing sequence or the reference oligonucleotide; $a_{i,j} + d_j$ is a binary variable representing whether the reference probing sequence with or without the introduced degenerate base and/or universal base is matched or mismatched at the $j^{th}$ position with the $i^{th}$ probing sequence or the reference oligonucleotide with or without the introduced degenerate base and/or universal base is matched or mismatched at the $j^{th}$ position with the $i^{th}$ oligonucleotide; $\{a_{i,j}+d_j\}$ represents a set including $a_{i,j}+d_j$ as elements; min $\{a_{i,j}+d_j\}$ represents a minimum value among the elements of the set $\{a_{i,j}+d_j\}$; and for all i, j represents application to all positions of all the probing sequences or the oligonucleotides.

2. The method according to claim 1, wherein the method further comprises, between the steps (a) and (b), (a-1) grouping the plurality of probing sequences or the plurality of oligonucleotides according to sequence identity to obtain a plurality of sequence patterns; wherein the step (c) is performed by introducing the degenerate base and/or universal base in a predetermined allowable number into the reference probing sequence or the reference oligonucleotide at the position(s) mismatched between the reference probing sequence or the reference oligonucleotide and the plurality of sequence patterns to be maximally matched with the plurality of sequence patterns, thereby preparing the oligonucleotide with the maximum target coverage.

3. The method according to claim 2, wherein the reference probing sequence is a probing sequence having the largest number of identical sequences among the plurality of probing sequences or a probing sequence of a sequence pattern having the largest number of probing sequences grouped into a sequence pattern among the plurality of sequence patterns; and wherein the reference oligonucleotide is an oligonucleotide having the largest number of identical sequences among the plurality of oligonucleotides or an oligonucleotide of a sequence pattern having the largest number of oligonucleotides grouped into a sequence pattern among the plurality of sequence patterns.

4. The method according to claim 2, wherein the step (c) is performed to achieve the following objective formula 2 together with satisfying the following constraint formulas 3 and 4:

$$\text{Max: } \sum_{i=1}^{r} p_i x_i \qquad \text{Objective formula 2}$$

wherein Max: represents maximization; $p_i$ is the number of probing sequences belonging to the $i^{th}$ sequence pattern of probing sequences or the number of oligonucleotides belonging to the $i^{th}$ sequence pattern of oligonucleotides; $x_i$ is a binary variable consisting of a non-selection value ($x_{non-sel}$) and a selection value ($x_{sel}$) for whether or not the $i^{th}$ sequence pattern of probing sequences or $i^{th}$ sequence pattern of oligonucleotides is selected; and i is a serial number of sequence patterns of probing sequences or oligonucleotides ranging from 1 to r;

$$\sum_{j=1}^{c} d_j \leq D_{Lim} \qquad \text{Constraint formula 3}$$

wherein $d_j$ is a binary variable consisting of a non-introduction value ($d_{non-int}$) and an introduction value ($d_{int}$) representing whether to introduce the degenerate base and/or universal base at the $j^{th}$ position of the reference probing sequence or the reference oligonucleotide; j is a serial number of positions of the reference probing sequence or the reference oligonucleotide ranging from 1 to c ; and $D_{Lim}$ is a limited number of the degenerate base and/or universal base introduced into the reference probing sequence or the reference oligonucleotide;

$$x_i \leq \min\{a_{i,j}+d_j\} \text{ for all } i,j \qquad \text{Constraint formula 4}$$

wherein $x_i$ is a binary variable consisting of a non-selection value ($x_{non-sel}$) and a selection value ($x_{sel}$) for whether or not the $i^{th}$ sequence pattern of probing sequences or $i^{th}$ sequence pattern of oligonucleotides is selected; $a_{i,j}$ is a binary constant representing whether a probing sequence belonging to the $i^{th}$ sequence pattern of probing sequences is matched or mismatched at the $j^{th}$ position with the reference probing sequence or an oligonucleotide belonging to the $i^{th}$ sequence pattern of oligonucleotides is matched or mismatched at the $j^{th}$ position with the reference oligonucleotide; $d_j$ is a binary variable consisting of a non-introduction value ($d_{non-int}$) and an introduction value ($d_{int}$) representing whether to introduce the degenerate base and/or universal base at the $j^{th}$ position of the reference probing sequence or the reference oligonucleotide; $a_{i,j}+d_j$ is a binary variable representing whether the reference probing sequence with or without the introduced degenerate base and/or universal base is matched or mismatched at the $j^{th}$ position with a probing sequence belonging to the $i^{th}$ sequence pattern of probing sequences or the reference oligonucleotide with or without the introduced degenerate base and/or universal base is matched or mismatched at the $j^{th}$ position with an oligonucleotide belonging to the $i^{th}$ sequence pattern of oligonucleotides; $\{a_{i,j}+d_j\}$ represents a set including $a_{i,j}+d_j$ as elements; min $\{a_{i,j}+d_j\}$ represents a minimum value among the elements of the set $\{a_{i,j}+d_j\}$; and for all i, j represents application to all positions of all the probing sequences or the oligonucleotides.

5. The method according to claim 4, wherein the non-selection value ($x_{non\text{-}sel}$) and the selection value ($x_{sel}$) of $x_i$ are 0 and 1, respectively.

6. The method according to claim 4, wherein the non-introduction value ($d_{non\text{-}int}$) and the introduction value ($d_{int}$) of $d_j$ are 0 and 1, respectively.

7. The method according to claim 4, wherein $D_{Lim}$ is 3.

8. The method according to claim 4, wherein the non-matching value and the matching value of $a_{i,j}$ are 0 and 1, respectively.

9. The method according to claim 1, wherein the reference probing sequence is a probing sequence having the largest number of identical sequences among the plurality of probing sequences or a probing sequence of a sequence pattern having the largest number of probing sequences grouped into a sequence pattern among the plurality of sequence patterns; and wherein the reference oligonucleotide is an oligonucleotide having the largest number of identical sequences among the plurality of oligonucleotides or an oligonucleotide of a sequence pattern having the largest number of oligonucleotides grouped into a sequence pattern among the plurality of sequence patterns.

10. The method according to claim 1, wherein the non-selection value ($x_{non\text{-}sel}$) and the selection value ($x_{sel}$) of $x_i$ are 0 and 1, respectively.

11. The method according to claim 1, wherein the non-introduction value ($d_{non\text{-}int}$) and the introduction value ($d_{int}$) of $d_j$ are 0 and 1, respectively.

12. The method according to claim 1, wherein $D_{Lim}$ is 3.

13. The method according to claim 1, wherein the non-matching value and the matching value of $a_{i,j}$ are 0 and 1, respectively.

14. The method according to claim 1, wherein the plurality of target nucleic acid sequences are a plurality of nucleic acid sequences having sequence similarity for one target nucleic acid molecule exhibiting genetic diversity.

15. The method according to claim 1, wherein the plurality of target nucleic acid sequences are a plurality of nucleic acid sequences corresponding to homologues of organisms having the same function, the same structure, or the same gene name.

16. A computer-implemented method for determining a probing region in a plurality of target nucleic acid sequences having sequence similarity, comprising:

(a) selecting one candidate probing region in a plurality of target nucleic acid sequences and providing sequences in the candidate probing region as a plurality of probing sequences;

(b) introducing a degenerate base and/or universal base in a predetermined allowable number into the plurality of probing sequences at a position(s) mismatched between the plurality of probing sequences such that the plurality of probing sequences are maximally matched with each other;

(c) determining the candidate probing region as a probing region for detecting all or a part of the plurality of target nucleic acid sequences when the maximum matching is not less than a predetermined coverage; and (d) preparing an oligonucleotide hybridizing with the probing region determined in step (c);

wherein the step (b) is performed to achieve the following objective formula 3 together with satisfying the following constraint formulas 5 and 6:

$$\text{Max:} \sum_{i=1}^{r} x_i \qquad \text{Objective formula 3}$$

wherein Max: represents maximization; $x_i$ is a binary variable consisting of a non-selection value ($x_{non\text{-}sel}$) and a selection value ($x_{sel}$) for whether or not the $i^{th}$ probing sequence of the plurality of probing sequences is selected; and i is a serial number of probing sequences ranging from 1 to r ;

$$\sum_{j=1}^{c} d_j \le D_{Lim} \qquad \text{Constraint formula 5}$$

wherein $d_j$ is a binary variable consisting of a non-introduction value ($d_{non\text{-}int}$) and an introduction value ($d_{int}$) representing whether to introduce the degenerate base and/or universal base at the $j^{th}$ position of the plurality of probing sequences; j is a serial number of positions of the probing sequence ranging from 1 to c ; and $D_{Lim}$ is a limited number of the degenerate base and/or universal base introduced into the plurality of probing sequences;

$$x_i \le \min\{a_{i,j}+d_j\} \text{ for all } i,j \qquad \text{Constraint formula 6}$$

wherein $x_i$ is a binary variable consisting of a non-selection value ($x_{non\text{-}sel}$) and a selection value ($x_{sel}$) for whether or not the $i^{th}$ probing sequence of the plurality of probing sequences is selected; $a_{i,j}$ is a binary constant representing whether the plurality of probing sequences is matched or mismatched with each other at the $j^{th}$ position; $d_j$ is a binary variable consisting of a non-introduction value ($d_{non\text{-}int}$) and an introduction value ($d_{int}$) representing whether to introduce the degenerate base and/or universal base at the $j^{th}$ position of the plurality of probing sequences; $a_{i,j}+d_j$ is a binary variable representing whether the plurality of probing sequences with or without the introduced degenerate base and/or universal base is matched or mismatched with each other at the $j^{th}$ position; $\{a_{i,j}+d_j\}$ represents a set including $a_{i,j}+d_j$ elements; min $\{a_{i,j}+d_j\}$ represents a minimum value among the elements of the set $\{a_{i,j}+d_j\}$; and for all i, j represents application to all positions of all the probing sequences.

17. The method according to claim 16, wherein the step (b) is performed by selecting one of the plurality of probing sequences as a reference probing sequence and introducing the degenerate base and/or universal base in a predetermined allowable number into the reference probing sequence at a position(s) mismatched between the reference probing sequence and the plurality of probing sequences to be maximally matched with the plurality of probing sequences.

18. The method according to claim 17, wherein the reference probing sequence is a probing sequence having the largest number of identical sequences among the plurality of probing sequences or a probing sequence of a sequence pattern having the largest number of probing sequences among the plurality of sequence patterns.

19. The method according to claim 17, wherein in the constraint formula 5, $d_j$ is a binary variable consisting of a non-introduction value ($d_{non-int}$) and an introduction value ($d_{int}$) representing whether to introduce the degenerate base and/or universal base at the $j^{th}$ position of the reference probing sequence; j is a serial number of positions of the reference probing sequence ranging from 1 to c ; and $D_{Lim}$ is a limited number of the degenerate base and/or universal base introduced into the reference probing sequence; and wherein in the constraint formula 6, $a_{i,j}$ is a binary constant representing whether the $i^{th}$ probing sequence is matched or mismatched at the $j^{th}$ position with the reference probing sequence; $d_j$ is a binary variable consisting of a non-introduction value ($d_{non-int}$) and an introduction value ($d_{int}$) representing whether to introduce the degenerate base and/or universal base at the $j^{th}$ position of the reference probing sequence; and $a_{i,j}+d_j$ is a binary variable representing whether the reference probing sequence with or without the introduced degenerate base and/or universal base is matched or mismatched at the $j^{th}$ position with the $i^{th}$ probing sequence.

20. The method according to claim 16, wherein the method further comprises, between the steps (a) and (b), (a-1) grouping the plurality of probing sequences according to sequence identity to obtain a plurality of sequence patterns; wherein the step (b) is performed by introducing the degenerate base and/or universal base in a predetermined allowable number into the plurality of probing sequences at a position(s) mismatched with each other in the plurality of sequence patterns such that the plurality of sequence patterns are maximally matched with each other; and wherein the step (c) is performed by determining the candidate probing region to which the sequence pattern belongs as a probing region for detecting all or a part of the plurality of target nucleic acid sequences when the maximum matching is not less than the predetermined coverage.

21. The method according to claim 20, wherein the step (b) is performed to achieve the following objective formula 4 together with satisfying the following constraint formulas 7 and 8:

$$\text{Max:} \sum_{i=1}^{r} p_i x_i \qquad \text{Objective formula 4}$$

wherein Max: represents maximization; $p_i$ is the number of probing sequences belonging to the $i^{th}$ sequence pattern of probing sequences; $x_i$ is a binary variable consisting of a non-selection value ($x_{non-sel}$) and a selection value ($x_{sel}$) for whether or not the $i^{th}$ sequence pattern of probing sequences is selected; and i is a serial number of sequence patterns of probing sequences ranging from 1 to r;

$$\sum_{j=1}^{c} d_j \le D_{Lim} \qquad \text{Constraint formula 7}$$

wherein $d_j$ is a binary variable consisting of a non-introduction value ($d_{non-int}$) and an introduction value ($d_{int}$) representing whether to introduce the degenerate base and/or universal base at the $j^{th}$ position of the probing sequence of the sequence pattern or the reference probing sequence; j is a serial number of positions of the probing sequence of the sequence pattern or the reference probing sequence ranging from 1 to c ; and $D_{Lim}$ is a limited number of the degenerate base and/or universal base introduced into the probing sequence of the sequence pattern or the reference probing sequence;

$$x_i \le \min\{a_{i,j}+d_j\} \text{ for all } i,j \qquad \text{Constraint formula 8}$$

wherein $x_i$ is a binary variable consisting of a non-selection value ($x_{non-sel}$) and a selection value ($x_{sel}$) for whether or not the $i^{th}$ sequence pattern of probing sequences is selected; is a binary constant representing whether probing sequences of each of the sequence patterns are matched or mismatched with each other at the $j^{th}$ position or a probing sequence of the $i^{th}$ sequence pattern is matched or mismatched at the $j^{th}$ position with the reference probing sequence; $d_j$ is a binary variable consisting of a non-introduction value ($d_{non-int}$) and an introduction value ($d_{int}$) representing whether to introduce the degenerate base and/or universal base at the $j^{th}$ position of the probing sequence of each of the sequence patterns or the reference probing sequence; $a_{i,j}+d_j$ is a binary variable representing whether the probing sequences of each of the sequence patterns with or without the introduced degenerate base and/or universal base are matched or mismatched with each other at the $j^{th}$ position or the reference probing sequence with or without the introduced degenerate base and/or universal base is matched or mismatched at the $j^{th}$ position with the probing sequence of the $i^{th}$ sequence pattern; $\{a_{i,j}+d_j\}$ represents a set including $a_{i,j}+d_j$ as elements; min $\{a_{i,j}+d_j\}$ represents a minimum value among the elements of the set $\{a_{i,j}+d_j\}$; and for all i, j represents application to all positions of all the probing sequences.

22. A non-transitory computer readable storage medium containing instructions to configure a processor to perform a method for preparing an oligonucleotide for detecting a plurality of target nucleic acid sequences having sequence similarity with a maximum target coverage, the method comprising:
(a) selecting each of sequences with sequence similarity in the same region of a plurality of target nucleic acid sequences as an oligonucleotide to prepare a plurality of oligonucleotides;
(b) selecting one of the plurality of oligonucleotides as a reference oligonucleotide;
(c) introducing a degenerate base and/or universal base in a predetermined allowable number into the reference oligonucleotide at a position(s) mismatched between the reference oligonucleotide and the plurality of oligonucleotides to be maximally matched with the plurality of oligonucleotides, (d) selecting as a sequence of an oligonucleotide a sequence of the reference oligonucleotide into which at least one of the degenerate base and/or the universal bases is introduced; and (e) preparing an oligonucleotide with a maximum target coverage with the sequence selected in step (d);
wherein the step (c) is performed to achieve the following objective formula 1 together with satisfying the following constraint formulas 1 and 2:

$$\text{Max:} \sum_{i=1}^{r} x_i \qquad \text{Objective formula 1}$$

wherein Max: represents maximization; $x_i$ is a binary variable consisting of a non-selection value ($x_{non-sel}$) and a selection value ($x_{sel}$) for whether or not the $i^{th}$ probing sequence of the plurality of probing sequences or $i^{th}$ oligonucleotide of the plurality of oligonucleotides is selected; and i is a serial number of probing sequences or oligonucleotides ranging from 1 to r;

$$\sum_{j=1}^{c} d_j \leq D_{Lim} \qquad \text{Constraint formula 1}$$

wherein $d_j$ is a binary variable consisting of a non-introduction value ($d_{non-int}$) and an introduction value ($d_{int}$) representing whether to introduce the degenerate base and/or universal base at the $j^{th}$ position of the reference probing sequence or the reference oligonucleotide; j is a serial number of positions of a reference probing sequence or a reference oligonucleotide ranging from 1 to c ; and $D_{Lim}$ is a limited number of the degenerate base and/or universal base introduced into the reference probing sequence or the reference oligonucleotide;

$$x_i \leq \min\{a_{i,j}+d_j\} \text{ for all } i,j \qquad \text{Constraint formula 2}$$

wherein $x_i$ is a binary variable consisting of a non-selection value ($x_{non-sel}$) and a selection value ($x_{sel}$) for whether or not the $i^{th}$ probing sequence of the plurality of probing sequences or $i^{th}$ oligonucleotide of the plurality of oligonucleotides is selected; $a^{i,j}$ is a binary constant representing whether the $i^{th}$ probing sequence is matched or mismatched at the $j^{th}$ position with the reference probing sequence or the $i^{th}$ oligonucleotide is matched or mismatched at the $j^{th}$ position with the reference oligonucleotide; $d_j$ is a binary variable consisting of a non-introduction value ($d_{non-int}$) and an introduction value ($d_{int}$) representing whether to introduce the degenerate base and/or universal base at the $j^{th}$ position of the reference probing sequence or the reference oligonucleotide; $a_{i,j}+d_j$ is a binary variable representing whether the reference probing sequence with or without the introduced degenerate base and/or universal base is matched or mismatched at the $j^{th}$ position with the $i^{th}$ probing sequence or the reference oligonucleotide with or without the introduced degenerate base and/or universal base is matched or mismatched at the $j^{th}$ position with the $i^{th}$ oligonucleotide; $\{a_{i,j}+d_j\}$ represents a set including $a_{i,j}+d_j$ as elements; min $\{a_{i,j}+d_j\}$ represents a minimum value among the elements of the set $\{a_{i,j}+d_j\}$; and for all i, j represents application to all positions of all the probing sequences or the oligonucleotides.

23. A non-transitory computer readable storage medium containing instructions to configure a processor to perform a method for determining a probing region in a plurality of target nucleic acid sequences having sequence similarity, the method comprising:
(a) selecting one candidate probing region in a plurality of target nucleic acid sequences and providing sequences in the candidate probing region as a plurality of probing sequences;
(b) introducing a degenerate base and/or universal base in a predetermined allowable number into the plurality of probing sequences at a position(s) mismatched between the plurality of probing sequences such that the plurality of probing sequences are maximally matched with each other;
(c) determining the candidate probing region as a probing region for detecting all or a part of the plurality of target nucleic acid sequences when the maximum matching is not less than a predetermined coverage; and
(d) preparing an oligonucleotide hybridizing with the probing region determined in step (c);
wherein the step (b) is performed to achieve the following objective formula 3 together with satisfying the following constraint formulas 5 and 6:

$$\text{Max: } \sum_{i=1}^{r} x_i \qquad \text{Objective formula 3}$$

wherein Max: represents maximization; $x_i$ is a binary variable consisting of a non-selection value ($x_{non-sel}$) and a selection value ($x_{sel}$) for whether or not the $i^{th}$ probing sequence of the plurality of probing sequences is selected; and i is a serial number of probing sequences ranging from 1 to r ;

$$\sum_{j=1}^{c} d_j \leq D_{Lim} \qquad \text{Constraint formula 5}$$

wherein $d_j$ is a binary variable consisting of a non-introduction value ($d_{non-int}$) and an introduction value ($d_{int}$) representing whether to introduce the degenerate base and/or universal base at the $j^{th}$ position of the plurality of probing sequences; j is a serial number of positions of the probing sequence ranging from 1 to c ; and $D_{Lim}$ is a limited number of the degenerate base and/or universal base introduced into the plurality of probing sequences;

$$x_i \leq \min\{a_{i,j}+d_j\} \text{ for all } i,j \qquad \text{Constraint formula 6}$$

wherein $x_i$ is a binary variable consisting of a non-selection value ($x_{non-sel}$) and a selection value ($x_{sel}$) for whether or not the $i^{th}$ probing sequence of the plurality of probing sequences is selected; $a_{i,j}$ is a binary constant representing whether the plurality of probing sequences is matched or mismatched with each other at the $j^{th}$ position; $d_j$ is a binary variable consisting of a non-introduction value ($d_{non-int}$) and an introduction value ($d_{int}$) representing whether to introduce the degenerate base and/or universal base at the $j^{th}$ position of the plurality of probing sequences; $a_{i,j}+d_j$ is a binary variable representing whether the plurality of probing sequences with or without the introduced degenerate base and/or universal base is matched or mismatched with each other at the $j^{th}$ position; $\{a_{i,j}+d_j\}$ represents a set including $a_{i,j}+d_j$ as elements; min $\{a_{i,j}+d_j\}$ represents a minimum value among the elements of the set $\{a_{i,j}+d_j\}$; and for all i, j represents application to all positions of all the probing sequences.

* * * * *

SEQUENCE LISTING

<160> NUMBER OF SEQ ID NOS: 20

<210> SEQ ID NO 1
<211> LENGTH: 20
<212> TYPE: DNA
<213> ORGANISM: Enterovirus

<400> SEQUENCE: 1
catcaggccc ctgaatgcgg                                                    20

<210> SEQ ID NO 2
<211> LENGTH: 20
<212> TYPE: DNA
<213> ORGANISM: Enterovirus

<400> SEQUENCE: 2
cttccgtccc ctgaatgcgt                                                    20

<210> SEQ ID NO 3
<211> LENGTH: 20
<212> TYPE: DNA
<213> ORGANISM: Enterovirus

<400> SEQUENCE: 3
cgtccggccc ctgaatgcgg                                                    20

<210> SEQ ID NO 4
<211> LENGTH: 20
<212> TYPE: DNA
<213> ORGANISM: Enterovirus

<400> SEQUENCE: 4
ccaccggccc ctgcatgcgg                                                    20

<210> SEQ ID NO 5
<211> LENGTH: 20
<212> TYPE: DNA
<213> ORGANISM: Enterovirus

<400> SEQUENCE: 5
ccaccggccc ctgaatgcgg                                                    20

<210> SEQ ID NO 6
<211> LENGTH: 20
<212> TYPE: DNA
<213> ORGANISM: Enterovirus

<400> SEQUENCE: 6
cctgcggccc ctgcttgcgg                                                    20

<210> SEQ ID NO 7
<211> LENGTH: 20
<212> TYPE: DNA
<213> ORGANISM: Enterovirus

<400> SEQUENCE: 7
cctcgggcac ctgaatgcgg                                                    20

-continued

```
<210> SEQ ID NO 8
<211> LENGTH: 20
<212> TYPE: DNA
<213> ORGANISM: Enterovirus

<400> SEQUENCE: 8
cctccagccc ctgaatgcgt                                              20

<210> SEQ ID NO 9
<211> LENGTH: 20
<212> TYPE: DNA
<213> ORGANISM: Enterovirus

<400> SEQUENCE: 9
cctccgtgct ctgaatgcgg                                              20

<210> SEQ ID NO 10
<211> LENGTH: 20
<212> TYPE: DNA
<213> ORGANISM: Enterovirus

<400> SEQUENCE: 10
cctccgggcc ctgattgctg                                              20

<210> SEQ ID NO 11
<211> LENGTH: 20
<212> TYPE: DNA
<213> ORGANISM: Enterovirus

<400> SEQUENCE: 11
cctccggacc ctgaatacgt                                              20

<210> SEQ ID NO 12
<211> LENGTH: 20
<212> TYPE: DNA
<213> ORGANISM: Enterovirus

<400> SEQUENCE: 12
cctccggcac ctgaatgggg                                              20

<210> SEQ ID NO 13
<211> LENGTH: 20
<212> TYPE: DNA
<213> ORGANISM: Enterovirus

<400> SEQUENCE: 13
cctccggccc cagaatgagg                                              20

<210> SEQ ID NO 14
<211> LENGTH: 20
<212> TYPE: DNA
<213> ORGANISM: Enterovirus

<400> SEQUENCE: 14
cctccggccc ccgaatgcgg                                              20

<210> SEQ ID NO 15
<211> LENGTH: 20
<212> TYPE: DNA
<213> ORGANISM: Enterovirus

<400> SEQUENCE: 15
```

-continued cctccggccc ctgaaagcgg                    20

<210> SEQ ID NO 16
<211> LENGTH: 20
<212> TYPE: DNA
<213> ORGANISM: Enterovirus

<400> SEQUENCE: 16
cctccggccc ctgaatggac                    20

<210> SEQ ID NO 17
<211> LENGTH: 20
<212> TYPE: DNA
<213> ORGANISM: Enterovirus

<400> SEQUENCE: 17
cctccggccc ctgaatgggc                    20

<210> SEQ ID NO 18
<211> LENGTH: 20
<212> TYPE: DNA
<213> ORGANISM: Enterovirus

<400> SEQUENCE: 18
cctccggccc ctgaatgagg                    20

<210> SEQ ID NO 19
<211> LENGTH: 20
<212> TYPE: DNA
<213> ORGANISM: Enterovirus

<400> SEQUENCE: 19
cctccggccc ctgaatgctg                    20

<210> SEQ ID NO 20
<211> LENGTH: 20
<212> TYPE: DNA
<213> ORGANISM: Enterovirus

<400> SEQUENCE: 20
cctccggccc ctgaatgcgg                    20